(12) United States Patent   (10) Patent No.: US 12,303,140 B2
Cundiff et al.                    (45) Date of Patent: May 20, 2025

(54) SURGICAL SYSTEMS AND METHODS INCLUDING CUTTING AND ALIGNING GUIDES FOR PERFORMING AN OSTEOTOMY

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Mark William Roberts, Jr., Gilbert, AZ (US); Eli W. Jacobson, Chandler, AZ (US); William J. Bush, Rockford, IL (US)

(73) Assignee: Fusion Orthopedics USA, LLC, Mesa, AZ (US)

( * ) Notice: Subject to any disclaimer, the term of this patent is extended or adjusted under 35 U.S.C. 154(b) by 69 days.

(21) Appl. No.: 18/394,184

(22) Filed: Dec. 22, 2023

(65) Prior Publication Data
US 2024/0350148 A1     Oct. 24, 2024

Related U.S. Application Data

(63) Continuation-in-part of application No. 18/304,236, filed on Apr. 20, 2023, now Pat. No. 11,963,686.

(51) Int. Cl.
  *A61B 17/15*    (2006.01)
  *A61B 17/17*    (2006.01)
  *A61B 17/68*    (2006.01)

(52) U.S. Cl.
  CPC ........ *A61B 17/151* (2013.01); *A61B 17/1775* (2016.11); *A61B 17/68* (2013.01); *A61B 17/152* (2013.01); *A61B 17/1703* (2013.01); *A61B 17/1732* (2013.01); *A61B 17/1735* (2013.01); *A61B 17/1739* (2013.01)

(58) Field of Classification Search
  CPC ... A61B 17/151; A61B 17/152; A61B 17/154; A61B 17/155; A61B 17/157; A61B 17/17; A61B 17/1703; A61B 17/1732; A61B 17/1735; A61B 17/1739; A61B 17/1775; A61B 17/1757; A61B 17/1764
  USPC .................................. 606/86 R, 87, 96, 97
  See application file for complete search history.

(56) References Cited

U.S. PATENT DOCUMENTS

| 6,711,432 | B1 | 3/2004 | Krause |
| 8,282,645 | B2 | 10/2012 | Lawrence |
| D695,402 | S | 12/2013 | Dacosta |
| 10,292,713 | B2 | 5/2019 | Fallin |
| 10,342,590 | B2 | 7/2019 | Bays |
| 10,376,268 | B2 | 8/2019 | Fallin |
| 10,561,426 | B1 | 2/2020 | Dayton |

(Continued)

OTHER PUBLICATIONS

Medetz Surgical Instruments: Orthopedic Surgical Instruments, Reese Osteotomy Guide https://www.medetzsurgical.com/428m10/osteotomy-guide-system.html.

*Primary Examiner* — Marcela I. Shirsat

(57) ABSTRACT

Surgical systems and methods for performing an osteotomy are disclosed herein. A surgical system includes a frame including a first section, second section, third section, fourth section, and a window. The surgical system can include a cut guide that can fit within the window and contact the first side, the second side, the third side, and the fourth side. The surgical system can include an aligner that can fit within the window and contact the first side, the second side, the third.

19 Claims, 25 Drawing Sheets

(56) References Cited

U.S. PATENT DOCUMENTS

| | | |
|---|---|---|
| 10,646,263 B2 | 5/2020 | Lamm |
| 10,849,670 B2 | 12/2020 | Santrock |
| 10,888,335 B2 | 1/2021 | Dayton |
| 10,898,211 B2 | 1/2021 | Fallin |
| 10,945,764 B2 | 3/2021 | Dayton |
| 11,058,546 B2 | 7/2021 | Hollis |
| 11,304,705 B2 | 4/2022 | Fallin |
| 11,304,735 B2 | 4/2022 | Sayger |
| 11,523,845 B2 | 12/2022 | Dayton |
| 11,547,425 B1* | 1/2023 | Lebrija ................. A61B 17/66 |
| 2007/0265634 A1 | 11/2007 | Weinstein |
| 2008/0172056 A1* | 7/2008 | Edwards ................ A61B 90/92 |
| | | 606/104 |
| 2009/0198244 A1 | 8/2009 | Leibel |
| 2010/0130981 A1* | 5/2010 | Richards ................ A61B 17/15 |
| | | 606/87 |
| 2012/0303033 A1 | 11/2012 | Weiner |
| 2013/0296872 A1* | 11/2013 | Davison ............... A61B 17/152 |
| | | 606/87 |
| 2014/0336658 A1 | 11/2014 | Luna |
| 2015/0305752 A1* | 10/2015 | Eash .................... A61B 17/157 |
| | | 606/88 |
| 2017/0042598 A1* | 2/2017 | Santrock ............. A61B 17/152 |
| 2017/0042599 A1 | 2/2017 | Bays |
| 2017/0079669 A1 | 3/2017 | Bays |
| 2018/0289423 A1 | 10/2018 | Singh |
| 2019/0336140 A1 | 11/2019 | Dacosta |
| 2021/0077192 A1 | 3/2021 | Perler |

* cited by examiner

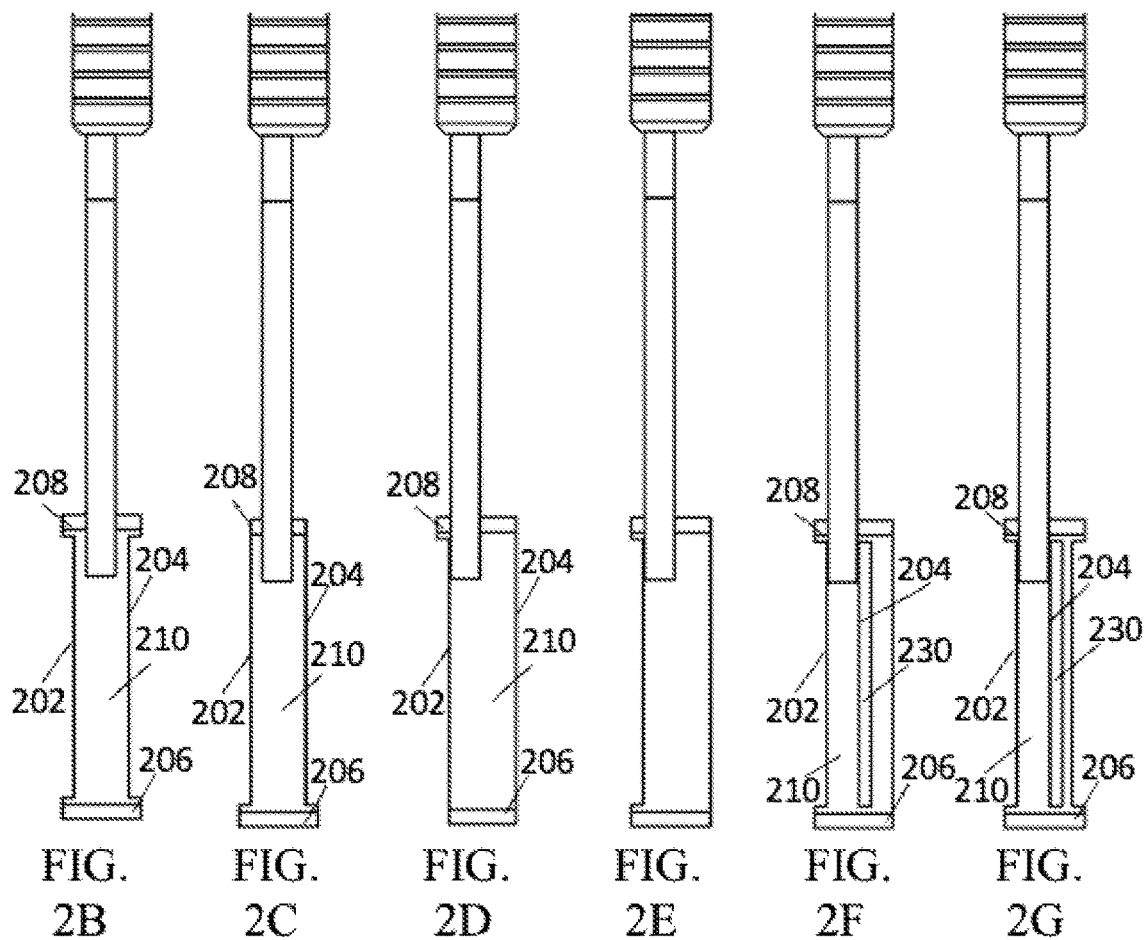
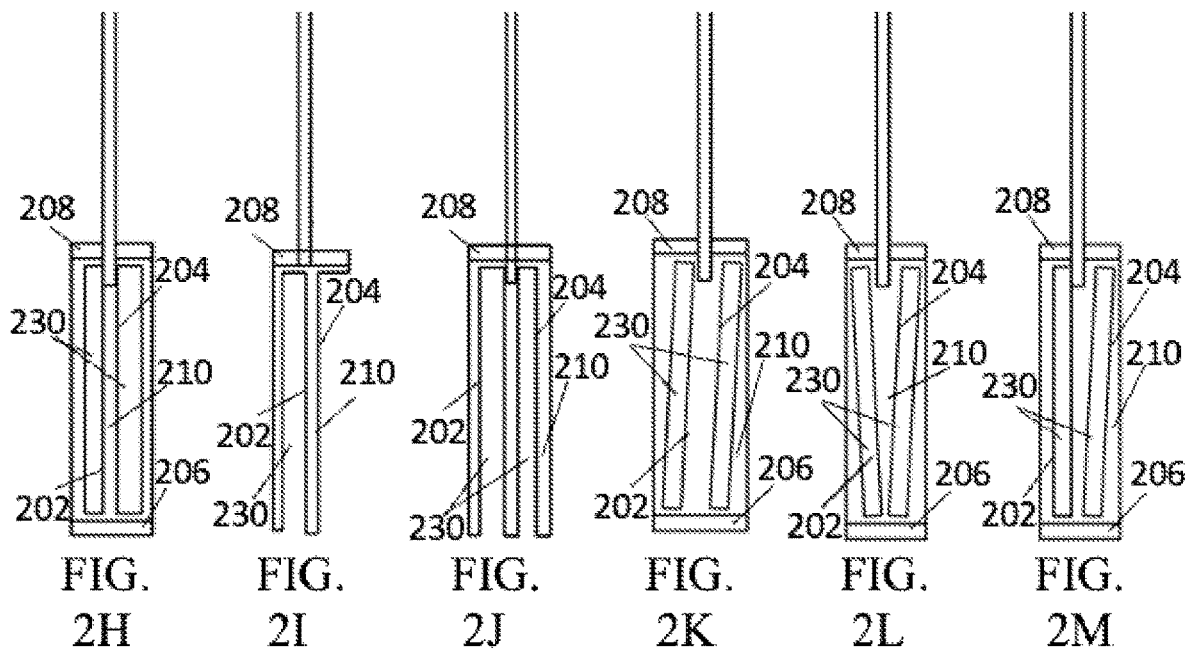

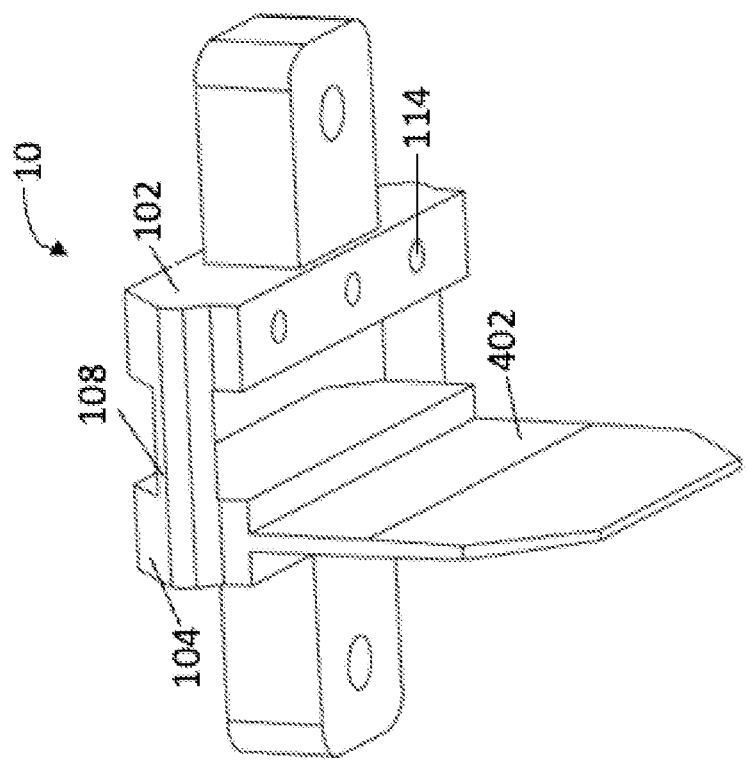
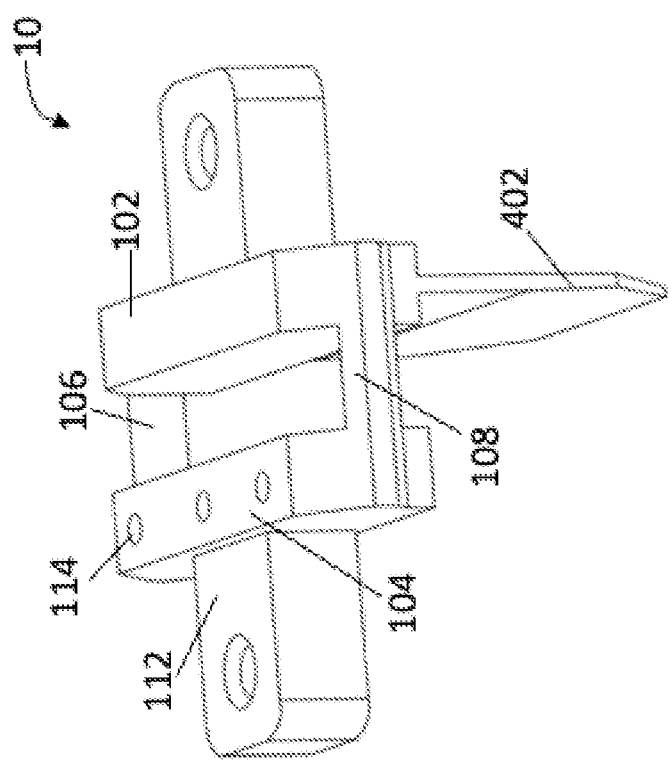

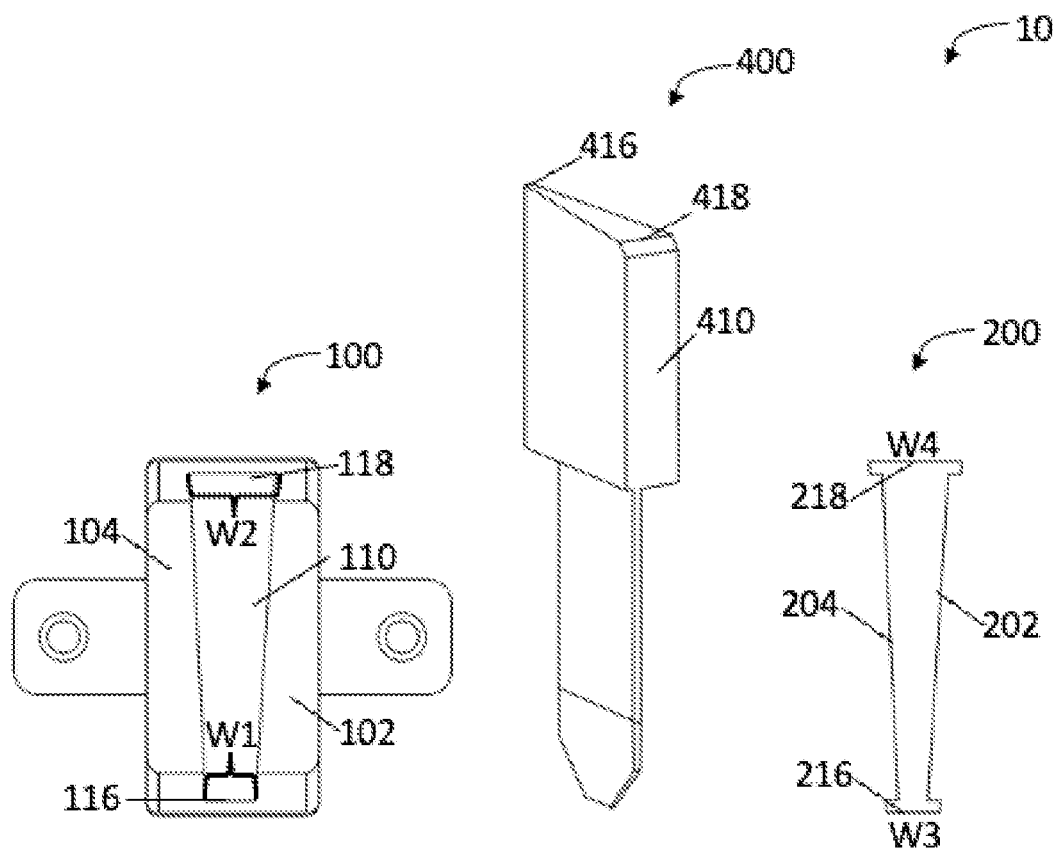
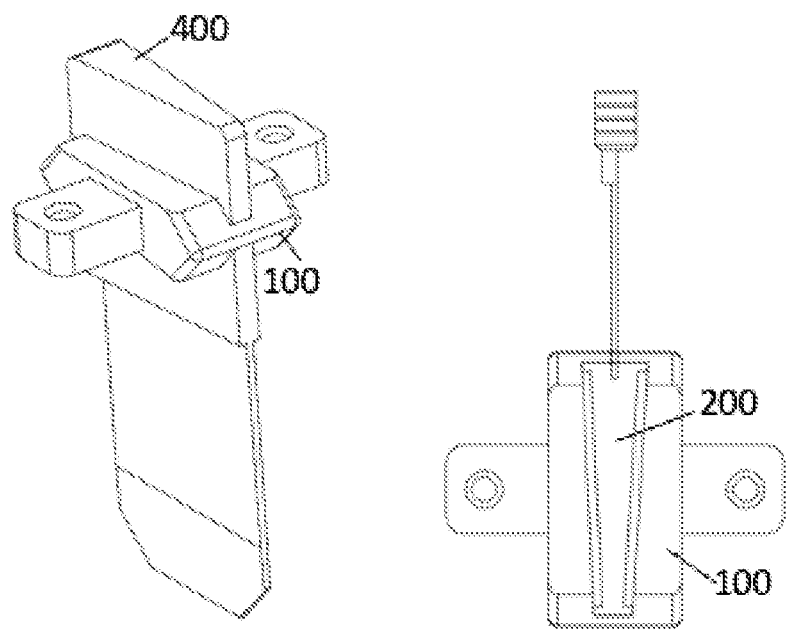
FIG. 7A     FIG. 7B     FIG. 7C
FIG. 7D     FIG. 7E

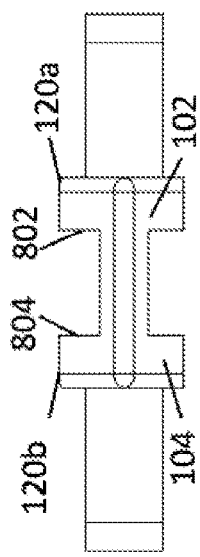
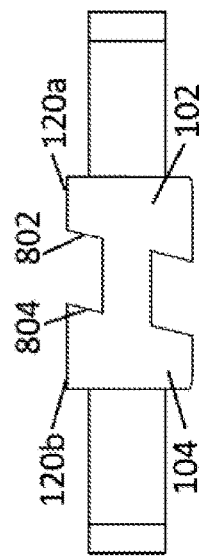
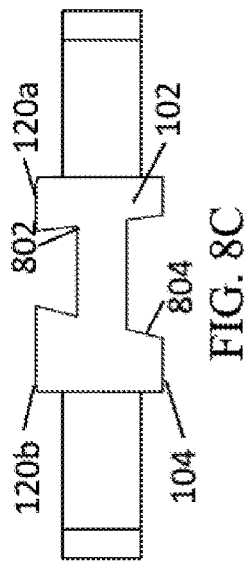
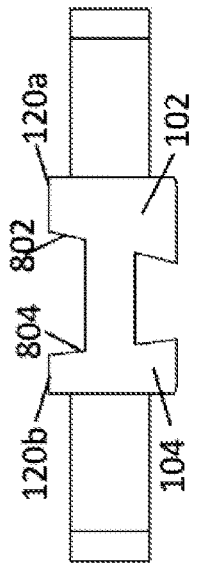
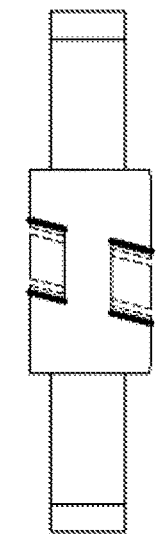
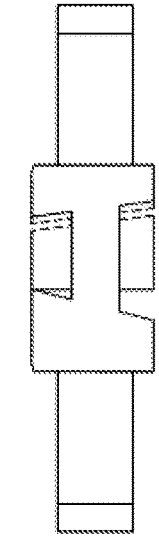
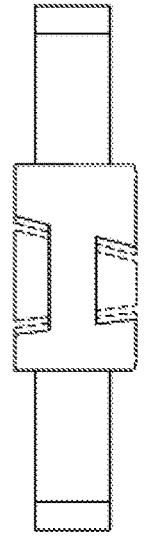
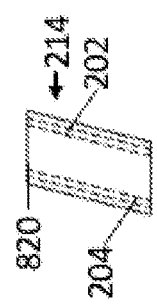

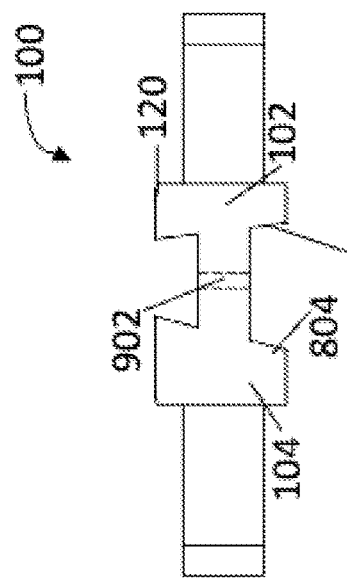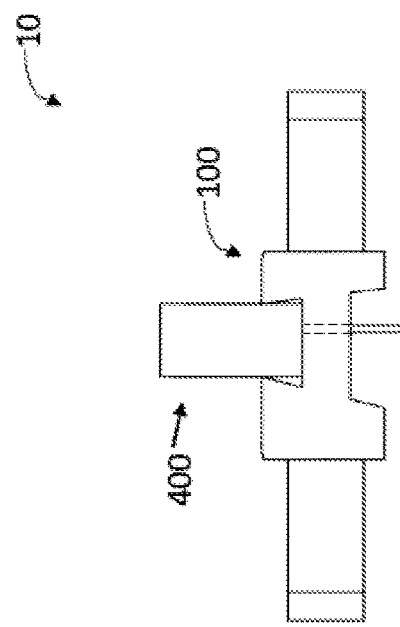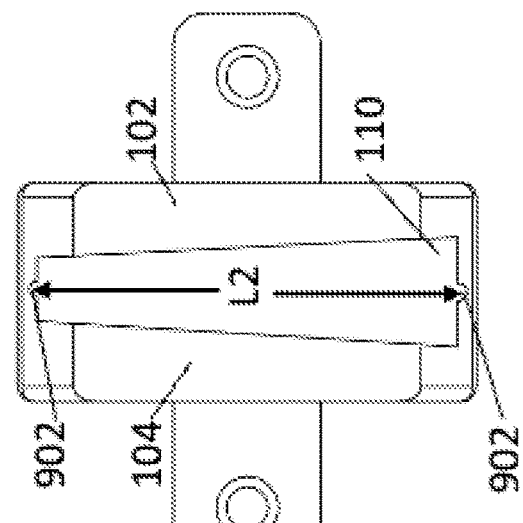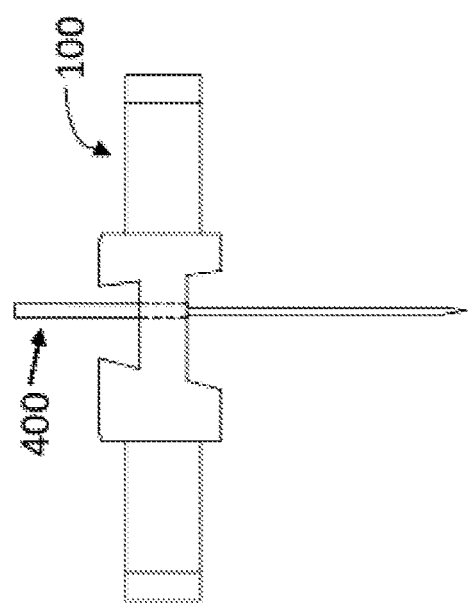

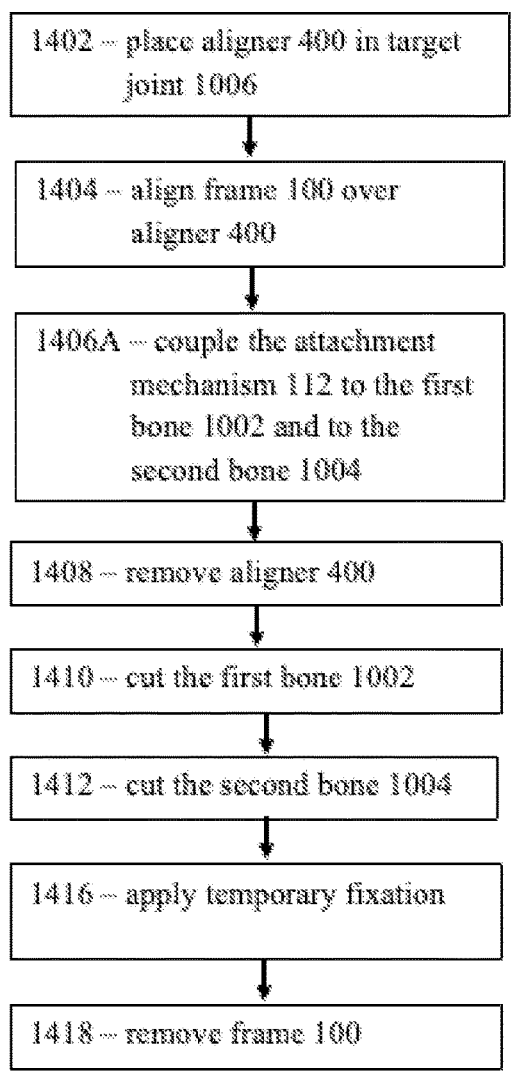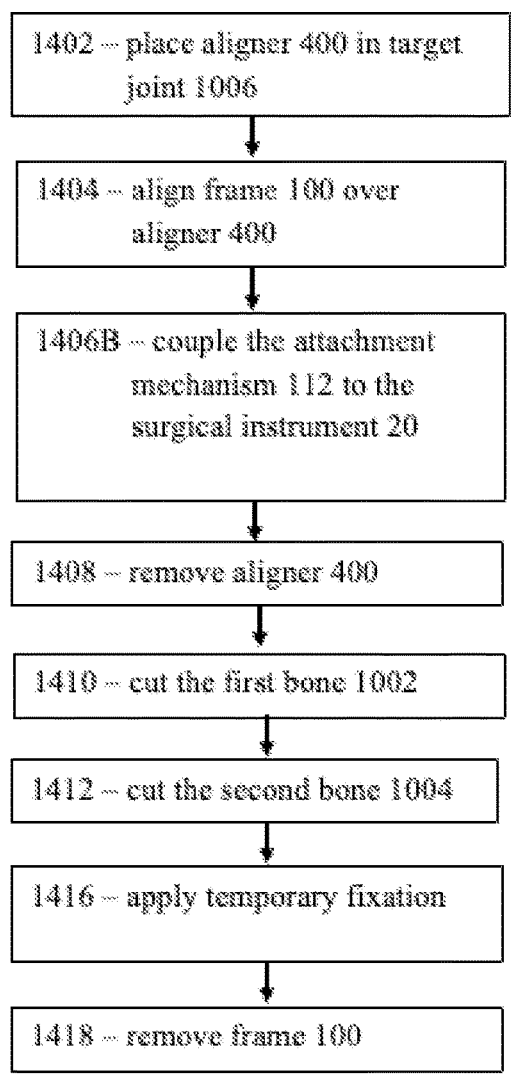
FIG. 14A
FIG. 14B

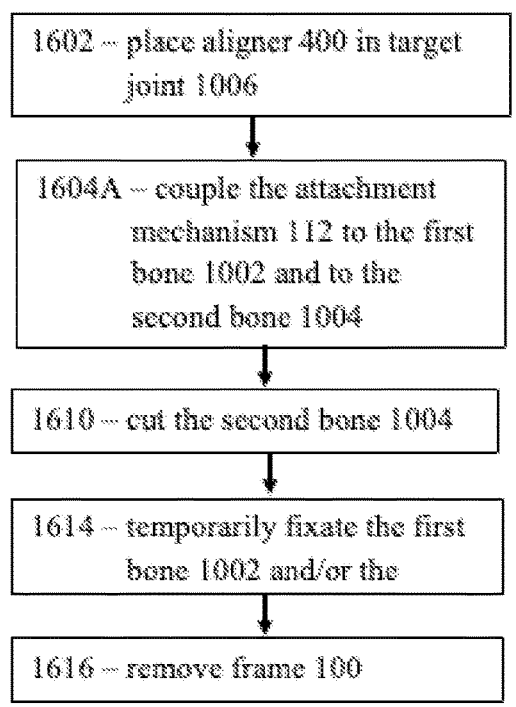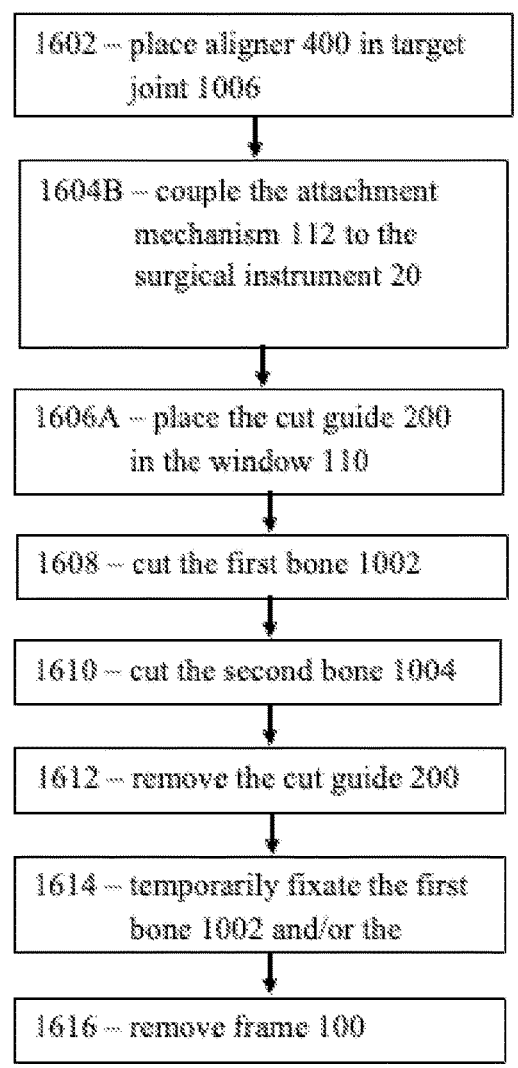

SURGICAL SYSTEMS AND METHODS INCLUDING CUTTING AND ALIGNING GUIDES FOR PERFORMING AN OSTEOTOMY

REFERENCE TO RELATED APPLICATION

This application is a Continuation-In-Part of and claims priority to U.S. patent application Ser. No. 18/304,236, now U.S. Pat. No. 11,963,686, filed on Apr. 20, 2023, the contents of which are incorporated herein by reference in its entirety.

FIELD OF THE TECHNOLOGY

The present technology relates generally to surgical cutting and aligning guides, and more particularly to, surgical instruments and systems for performing an osteotomy.

BACKGROUND

Surgical cut guides can be helpful in performing an osteotomy. However, they can be difficult to align properly and can restrict visibility of and access to the osteotomy site. This restriction can require multiple installations and removals of a cutting and/or aligning guide which can add time to the surgical procedure and add damage to a patient's bone. The goal in an osteotomy is often to remove as little bone as possible to prevent negative surgical outcomes. Some cut guides only allow for a fixed amount of bone removal, which may or may not be ideal for a specific patient.

SUMMARY

A surgical system comprising a first section, a second section, a third section and a fourth section, which can define a window. The first section and the second section can be separated by a first width. The first section can be configured to align with a first bone. The second section can be configured to align with a second bone. The window includes a size that can be configured to span a target joint between the first and second bones when the first section is aligned with the first bone and the second section is aligned with the second bone to provide surgical access to the target joint. The surgical system can further comprise at least one attachment mechanism that can be coupled to at least one of the first section, the second section, the third section, and the fourth section. The attachment mechanism can be configured to secure the surgical system to the first bone, the second bone, and/or a surgical jig.

The surgical system can further comprise a cut guide. The cut guide can comprise a head. The head can comprise a first member and a second member. The first member can be perpendicular to the second member. The head can further comprise a third member that can be parallel to the first member and perpendicular to the second member. The first member can comprise a second width. The second width can be less than the first width which allows the head to fit within the window and contact the first section, the second section, the third section, and the fourth section. The second member can comprise a fourth width that is less than the second width and is centered within the second width. The cut guide can further comprise a placement device that can be comprised of at least one of a handle, a handlebar, a magnet, a bar, a knob, a hold, a grip, a shaft, and a tab.

The surgical system can further comprise an aligner. The aligner can be detachable. The aligner can comprise a grip. The grip can comprise a grip depth that is less than the first width such that the grip fits within the window and contacts the first section, the second section, the third section, and the fourth section. The grip can at least partially comprise a high friction surface. The aligner can further comprise a shim. The shim can comprise a shim depth that is less than or equal to the grip depth. The shim depth can be uniform or at least partially tapered. The shim can be centered or off-centered on the grip.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which:

FIGS. 2B through 2M are top views of schematic diagrams illustrating various embodiments of the surgical system including the cut guide;

FIGS. 6A and 6B are schematic diagrams illustrating various embodiments of the surgical system including the frame and an integral aligner;

FIGS. 7A through 7E are schematic diagrams illustrating various embodiments of the surgical system including the frame, the cut guide, and/or the aligner;

FIGS. 8A through 8D are the front view of schematic diagrams illustrating various embodiments of the frame;

FIGS. 8E through 8G are the front view of schematic diagrams illustrating various embodiments of the cut guide;

FIGS. 8H through 8J are the front view of schematic diagrams illustrating various embodiments of the surgical system including the frame, and the cut guide;

FIGS. 9A through 9D are schematic diagrams illustrating various embodiments of the surgical system including the frame and/or the aligner;

FIGS. 14A and 14B are flow charts illustrating embodiments of performing an osteotomy with the frame and the aligner;

FIGS. 16A through 16C are flow charts illustrating embodiments of performing an osteotomy with the frame with an integral aligner.

DETAILED DESCRIPTION OF THE DRAWINGS

Figure 1C:
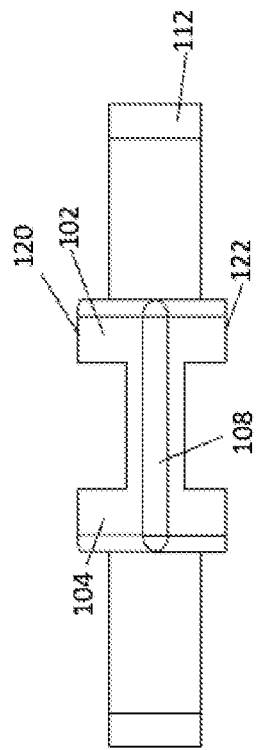
FIG. 1C is a front view of a schematic diagram illustrating an embodiment of the surgical system including the frame.
Figure 1D:
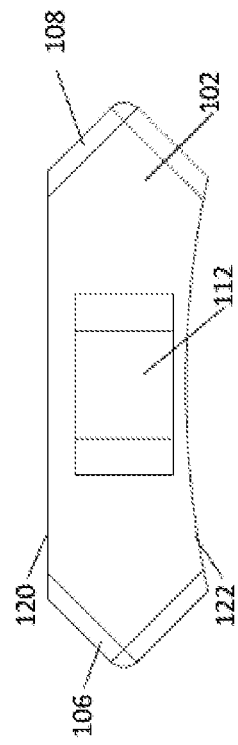
FIG. 1D is a side view of a schematic diagram illustrating an embodiment of the surgical system including the frame.
Figure 1A:
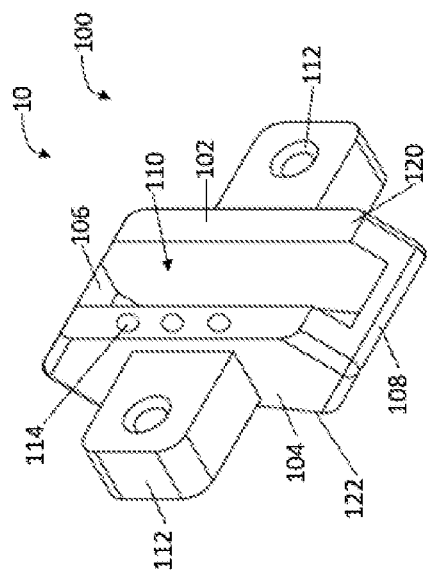
FIG. 1A is an isometric view of a schematic diagram illustrating an embodiment of a surgical system including a frame.
Figure 1B:
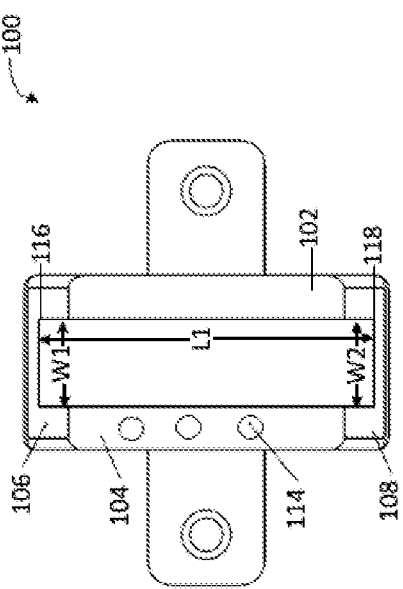
FIG. 1B is a top view of a schematic diagram illustrating an embodiment of the surgical system including the frame.
Figure 1E:
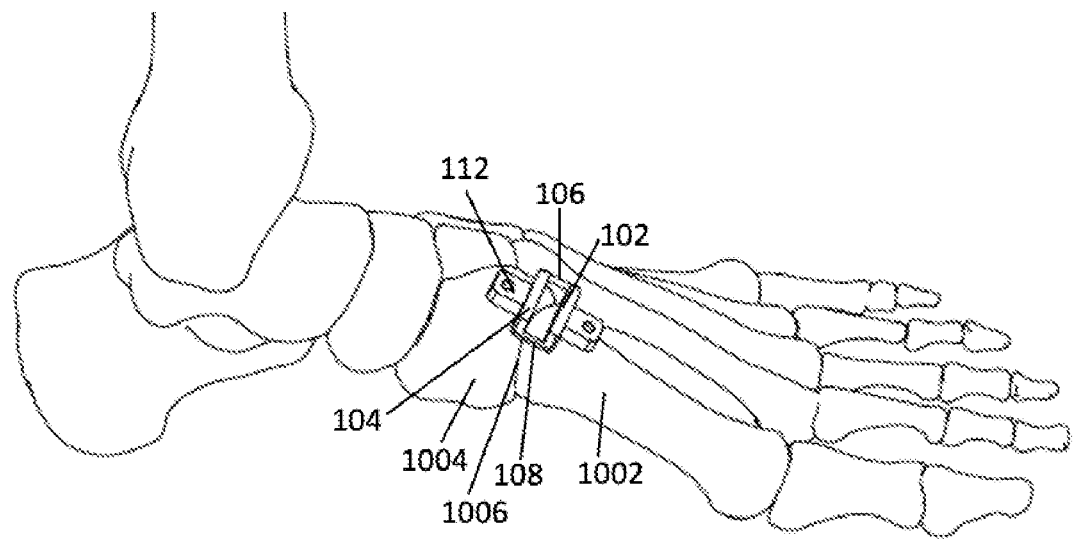
FIGS. 1E through 1J are a schematic diagrams illustrating various embodiments of the surgical system including the frame.
Figure 1F:
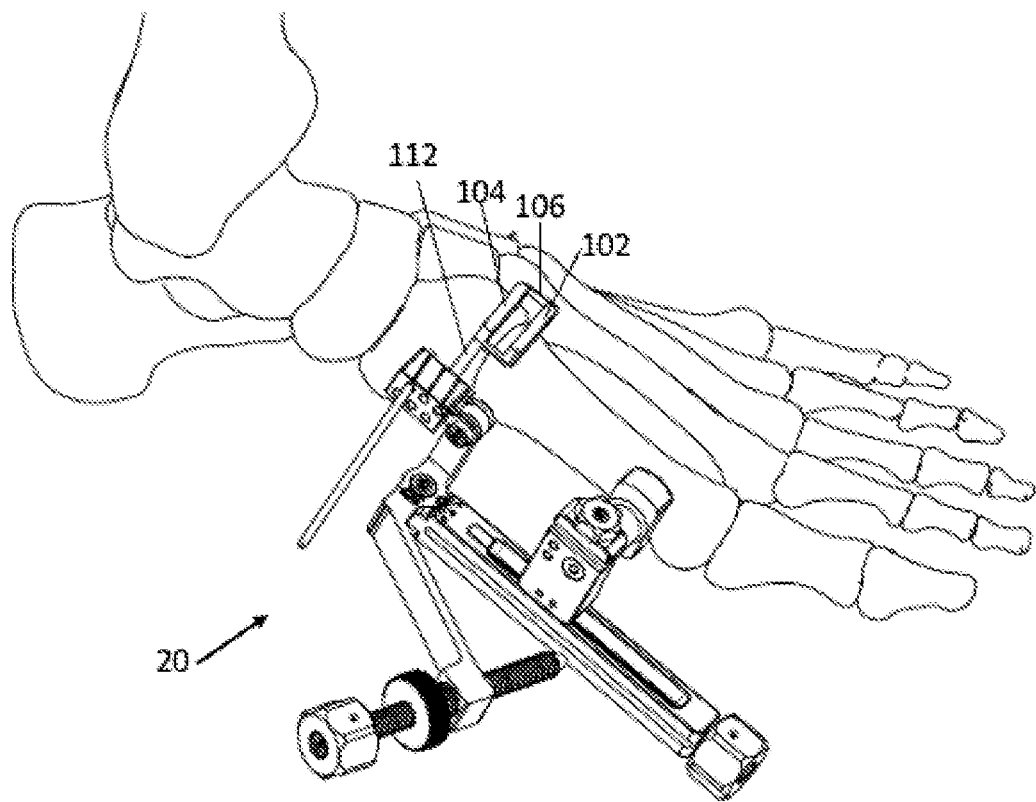
Figure 1I:
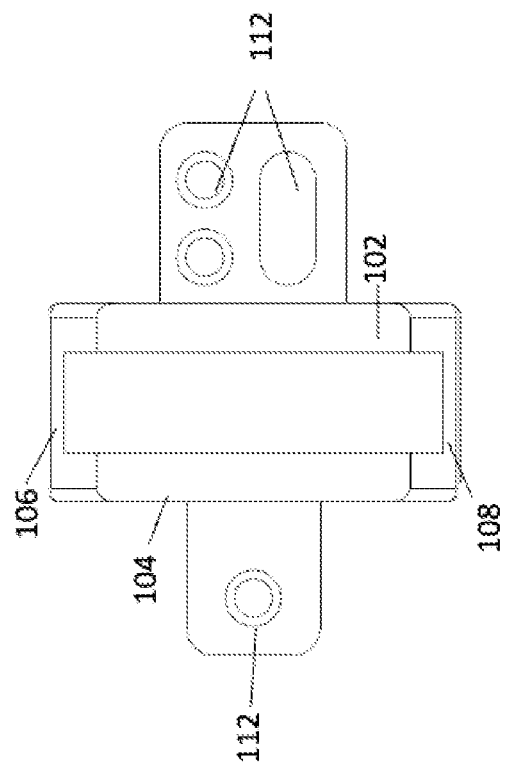
Figure 1G:
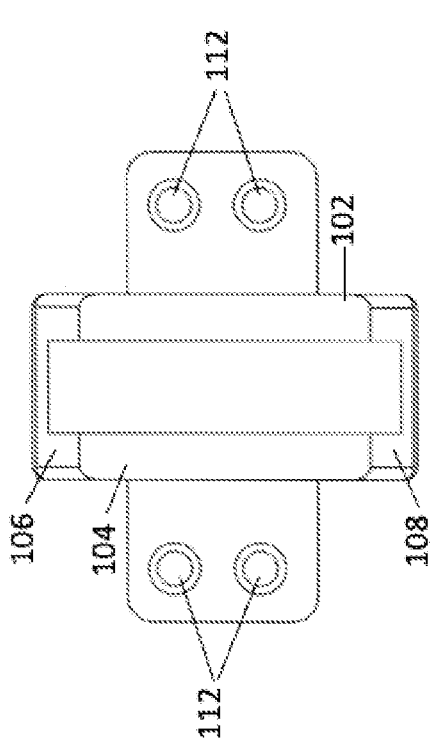
Figure 1H:
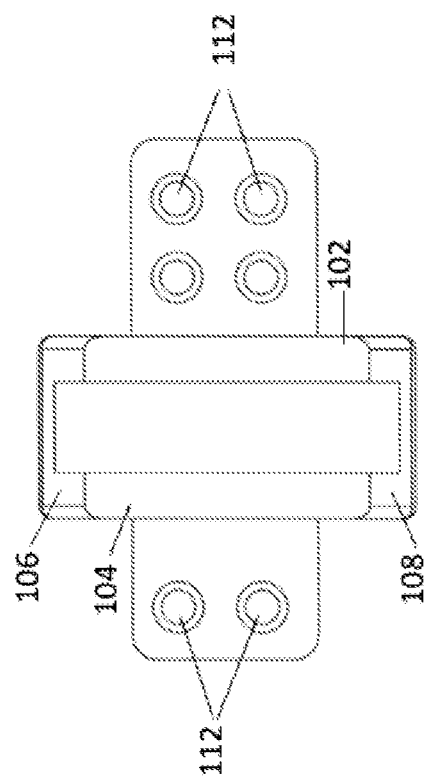
Figure 1J:
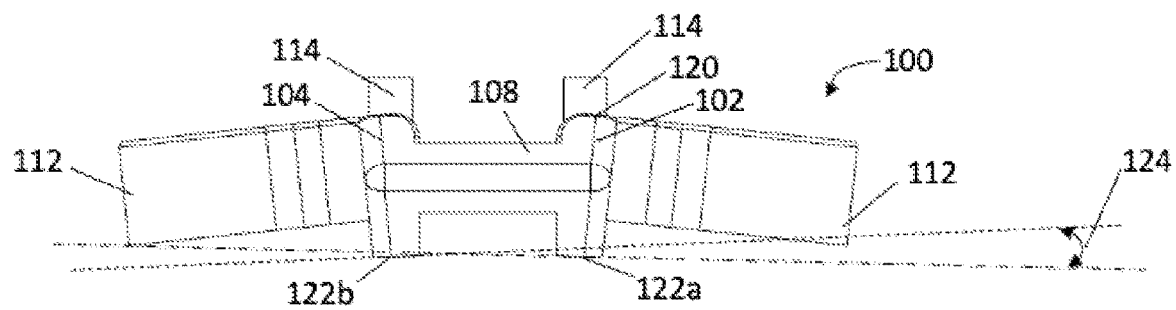
Figure 1K:
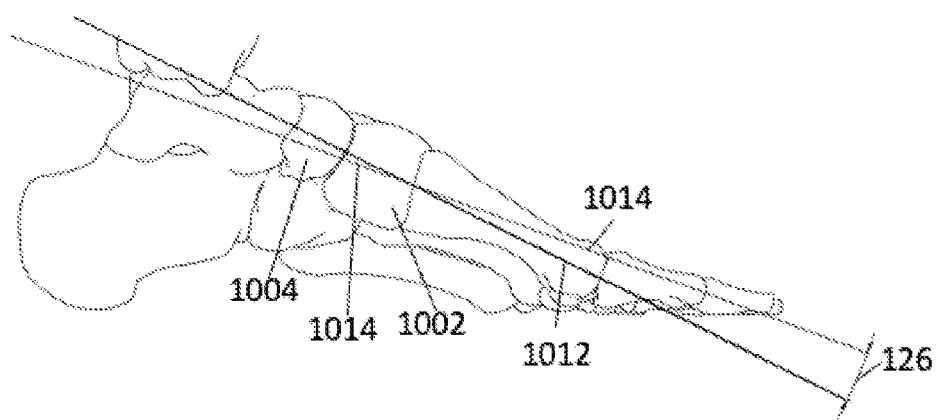
FIG. 1K is a side view of a schematic diagram illustrating a declination angle.
Figure 1L:
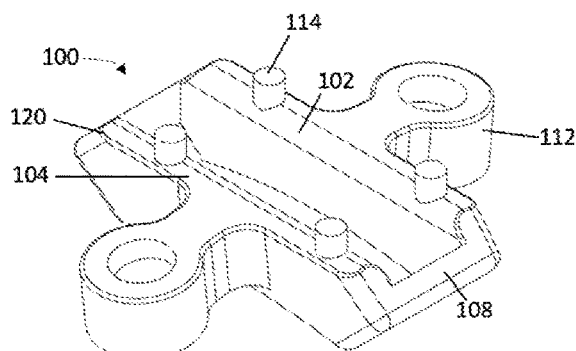
FIGS. 1L and 1M are a schematic diagrams illustrating various embodiments of the surgical system including the frame.
Figure 1M:
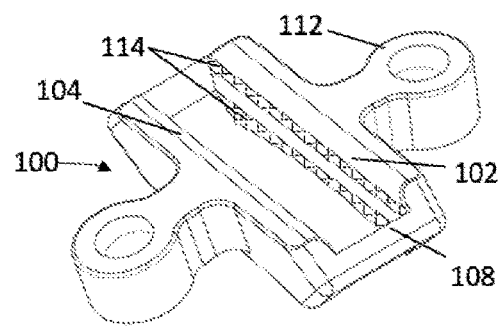

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

In addition, as used herein, the term "first bone" can refer to a bone or bone portion. The term "second bone" can refer to a bone that is a different bone than the first bone, or it can refer to a different portion of the same bone as the first bone. The term "joint" can refer to the place where two bones meet, and/or the ends of those bones, such as in the case of the first bone and the second bone being different bones. The term "joint" can refer to a fracture, such as in the case where "first bone" refers to a first bone portion and "second bone" refers to a different portion of the same bone. The term "joint" can also refer to the desired location of an osteotomy.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. Aspects of the embodiments are described below with reference to schematic flowchart diagrams and/or schematic block diagrams of methods, apparatuses, and systems according to embodiments. The schematic flowchart diagrams and/or schematic block diagrams in the Figures illustrate the structure, functionality, and operation of possible implementations of apparatuses, systems, and methods according to various embodiments.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment.

The present technology may include any type of surgical system and is not limited to the style of surgical system depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1A through 9C are schematic diagrams illustrating various views and/or embodiments of a surgical system 10. In various embodiments, the surgical system 10 can be utilized to perform a wedge-shaped osteotomy, straight-cut osteotomy, and/or parallel-cut osteotomy.

The surgical system 10 may be constructed of any suitable material. In various embodiments, the surgical system 10 is constructed of a material that can be sterilized, and/or a material that is sterilized. In some embodiments, the surgical system 10 includes stainless steel, radio-opaque, titanium, titanium alloy, plastic, and/or aluminum, among other suitable materials that are possible and contemplated herein. In additional or alternative embodiments, the surgical system 10 includes surgical grade stainless steel, among other suitable surgical grade materials that are possible and contemplated herein.

Referring now to FIGS. 1A through 1M. At least in the illustrated embodiment, the surgical system 10 includes, among other features, a frame 100. The frame 100 includes, among other features, a first section 102, a second section 104, a third section 106, and a fourth section 108 which form a window 110 therebetween. The sections can form a single window, or a plurality of windows. The window includes a window first end 116 with a first window width W1 and a window second end 118 with a second window width W2. The frame 100 and/or window 110 may include any suitable dimensions that can assist in performing an osteotomy. In various embodiments, the frame 100 and/or window 110 includes dimensions that are suitable for performing an osteotomy on a human. In various embodiments, the frame 100 and/or window 110 includes dimensions that are suitable for performing an osteotomy on a non-human. In various embodiments, the frame 100 and/or window 110 includes dimensions that are suitable for performing a Lapidus procedure, a metadductus procedure, metatarsus adductus, talar-navicular fusion, calcaneal cuboid fusion, and/or shortening osteotomies, among other procedures that are possible and contemplated herein.

The first window width W1 and the second window width W2 can be equal wherein the first section 102 and the second section 104 can be parallel and separated by the width W1 and/or W2. In some embodiments the first window width W1 can be greater than the second window width W2. In other embodiments the second window width W2 can be greater than the first window width W1. In some embodiments the first window width W1 can be in the range of 3 mm to 12 mm, among other ranges that are suitable and contemplated herein. In some embodiments the first window width W1 can be 6 mm. In some embodiments the first window width W1 is greater than 6 mm, and in other embodiments the first window width W1 is less than 6 mm. In some embodiments the second window width W2 can be in the range of 3 mm to 12 mm, among other ranges that are suitable and contemplated herein. In some embodiments the second window width W2 can be 6 mm. In some embodiments the second window width W2 is greater than 6 mm, and in other embodiments the second window width W2 is less than 6 mm.

The third section 106 and the fourth section 108 can be parallel and separated by a length L1. The length L1 can be in the range of 10 mm to 23 mm, among other ranges that are suitable, each of which is contemplated herein. In some embodiments the length L1 is 21 mm. In various embodiments the length L1 can be greater than 21 mm, and in other embodiments the length L1 can be less than 21 mm.

In various embodiments the first section 102, the second section 104, the third section 106, and/or the fourth section 108 can be contoured to conform to the shape of at least one bone (e.g., see FIG. 1D), for example, a metatarsal, a cuneiform, a talus, a navicular, a cuboid, and/or a calcaneus, among other shapes and/or bones that are possible and contemplated herein. In various embodiments a frame top 120 and a frame bottom 122 are the same shape, making the frame reversible. In various embodiments the frame top 120 and the frame bottom 122 are different shapes which may assist in proper placement and/or alignment of the frame 100 over a target joint 1006.

The frame 100 can include an attachment mechanism 112 which can be coupled to at least one of the first section 102, the second section 104, the third section 106, and/or the fourth section 108. In some embodiments the attachment mechanism 112 is configured to couple the frame 100 to a first bone 1002 and/or a second bone 1004 (e.g., see FIG. 1E). In some embodiments the attachment mechanism 112 is configured to couple the frame 100 to a surgical instrument 20 (e.g., see FIG. 1F), such as a surgical jig, a bone positioner, a clamp, and/or a bone positioning device, among other instruments that are possible and contemplated herein. In some embodiments the attachment mechanism 112 is removably couplable to the surgical instrument 20. In other embodiments the attachment mechanism 112 is integral with the surgical instrument 20. In further embodiments the attachment mechanism is non-removably coupled to the surgical instrument 20. The attachment mechanism 112 can include a platform, an extension, an aperture, a slot, a clamp, a pin, a k-wire, an olive wire, a blade, and/or a detent, among other devices that are possible and contemplated herein.

The first bone 1002 can be any bone or bone portion, for example the first bone 1002 can be a cuneiform, part of a cuneiform, a metatarsal, part of a metatarsal, a talus, part of a talus, a cuboid, part of a cuboid, a navicular, part of a navicular, calcaneus, part of a calcaneus, etc., among other bones that are possible and contemplated herein. The second bone 1004 can be any bone or bone portion, for example the second bone can be the cuneiform, part of the cuneiform, metatarsal, part of the metatarsal, talus, part of the talus, cuboid, part of the cuboid, navicular, part of the navicular, calcaneus, or part of the calcaneus, etc., among other bones that are possible and contemplated herein. In at least one embodiment, the first bone 1002 is not the same bone and/or bone portion as the second bone 1004.

The frame 100 can include at least one radiograph positioning tool 114. The radiograph positioning tool 114 can be one or more apertures, one or more posts, one or more extensions, one or more fins, one or more extensions, and/or one or more bars, among other devices that are possible and contemplated herein. The radiograph positioning tool 114 can be a combination of one or more apertures (e.g., see FIG. 1A), one or more posts (e.g., see FIG. 1L), one or more extensions, one or more fins, one or more bars (e.g., see FIG. 1M), and/or other devices that are possible and contemplated herein. The radiograph positioning tool 114 can be coupled to at least one portion of the frame 100, such as, the first section 102, the second section 104, the third section 106, the fourth section 108, and/or the attachment mechanism 112, among other portions of the frame that are possible and contemplated herein. The radiograph positioning tool 114 can be any shape or configuration, such as, a smiley face, emoji, icon, text, circular/cylindrical, square/cubic, rectangular/cuboidal, among other shapes that are possible and contemplated herein.

In various embodiments the frame may include a declination angle 124 (e.g., see FIG. 1J) wherein the frame bottom 122a of the first section 102 may be at an angle relative to the frame bottom 122b of the second section 104. The declination angle 124 may be the same as an angle 126 formed between a longitudinal axis 1012 of a first bone 1002 and a longitudinal axis 1014 of a second bone 1004 (e.g., see FIG. 1K), which may allow the frame bottom 122 to conform more closely to the anatomy of at least one bone. In some embodiments the declination angle 124 can be in the range of about zero degrees (0° or not angled) to about twenty degrees (20°) among other ranges of degree and/or degrees that are possible and contemplated herein. In some embodiments the declination angle 124 can be in the range of about five degrees (5°) to about twenty degrees (20°) among other ranges of degree and/or degrees that are possible and contemplated herein. In at least one embodiment the declination angle 124 can be twelve degrees (12°). In other embodiments the declination angle 124 can be more than 12°. In further embodiments the declination angle can be less 12°.

Figure 2A:
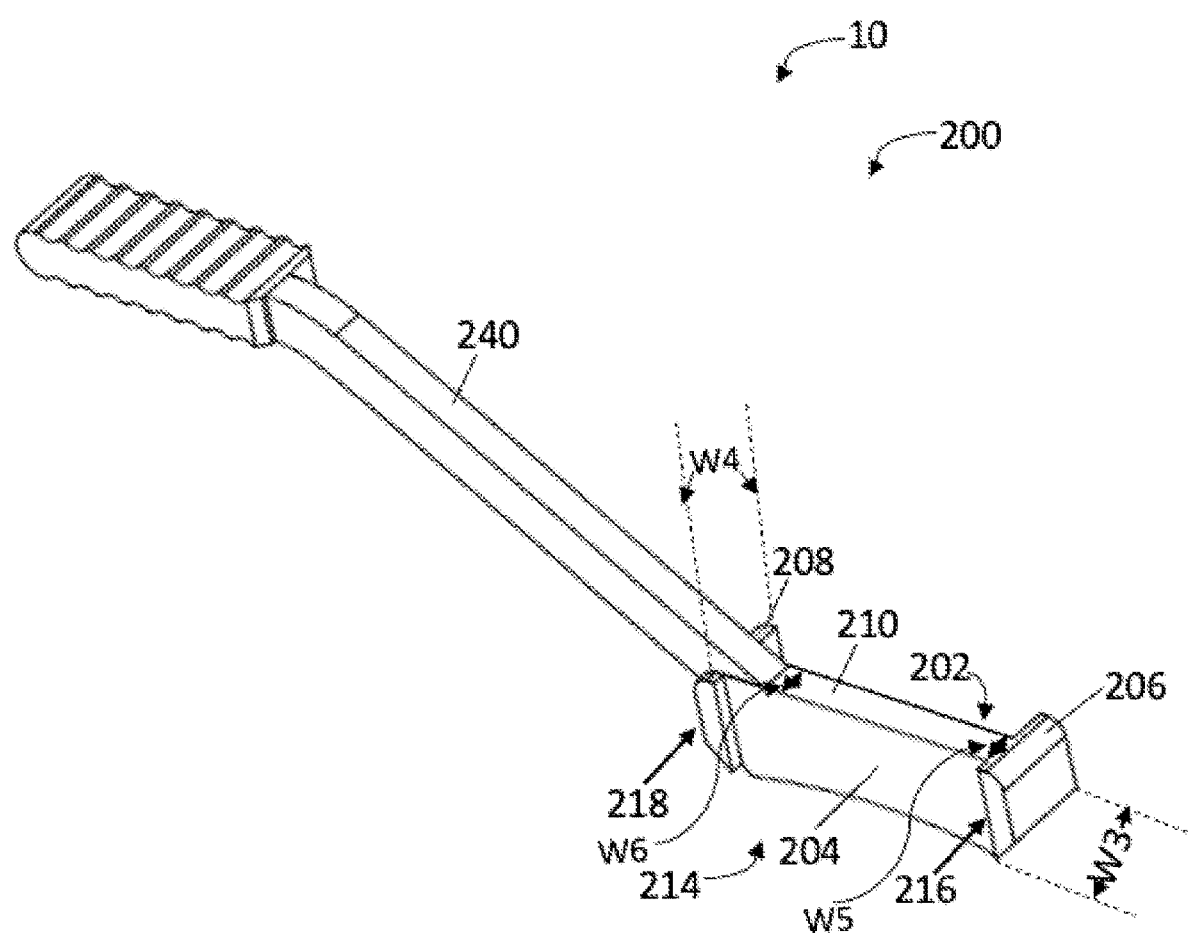
FIG. 2A is a schematic diagram illustrating an embodiment of the surgical system including a cut guide.
Figure 2N:
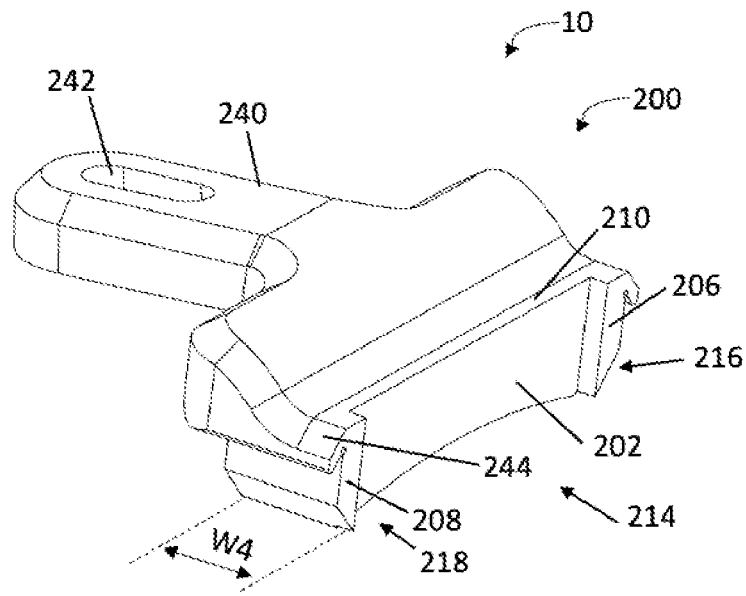
FIGS. 2N and 2O are schematic diagrams illustrating various embodiments of the surgical system including the cut guide.
Figure 2O:
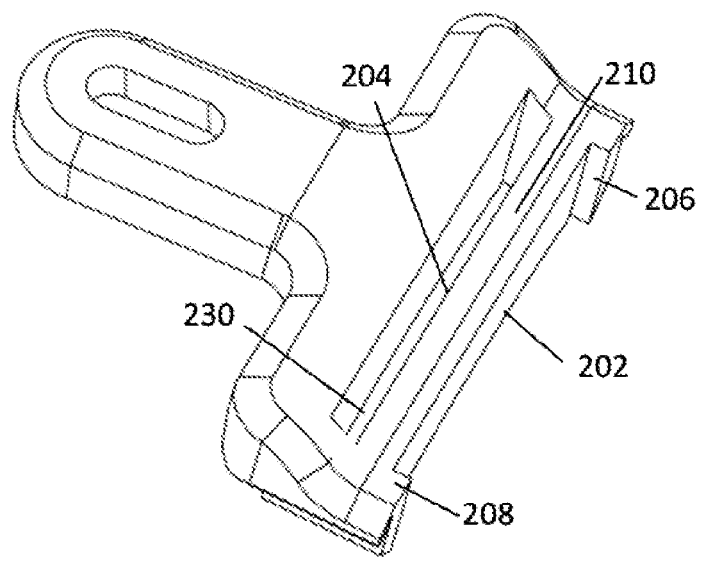
Figure 3C:
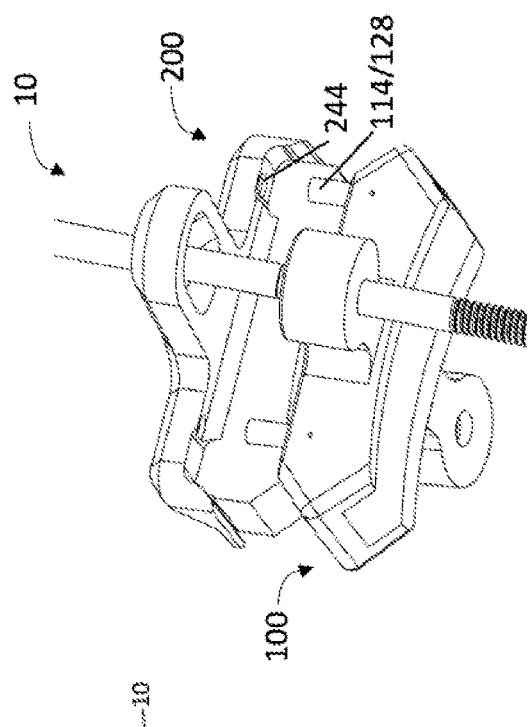
FIG. 3C is a schematic diagram illustrating an embodiment of the surgical system including at least a portion of the cut guide being inserted into the window.
Figure 3D:
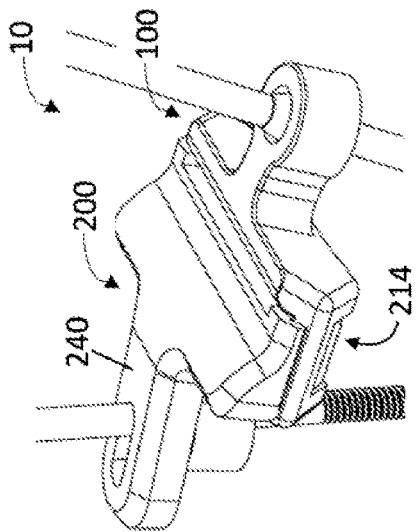
FIGS. 3A, 3B, 3D, and 3E are schematic diagrams illustrating various embodiments of the surgical system including at least a portion of the cut guide inserted into the frame.
Figure 3B:
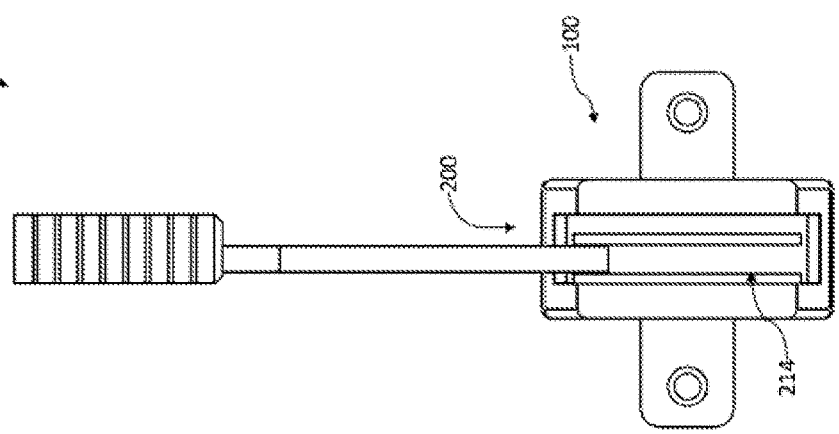
Figure 3A:
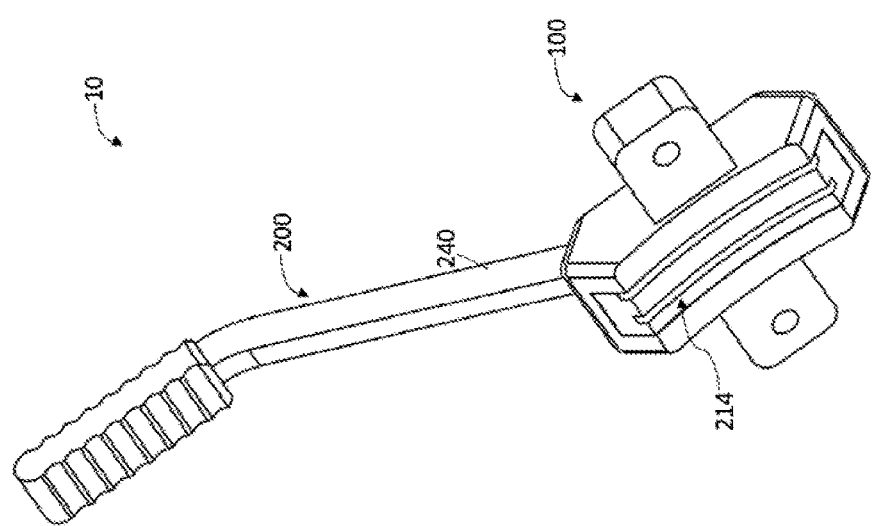

Referring now to FIGS. 2A through 2O. The surgical system 10 can include, among other features, a cut guide 200. The cut guide 200 can include, among other features, a head 214. The head 214 can include a first end 216 with a first head width W3 and a second end 218 with a second head width W4. The first head width W3 can be the same as, or different from, the second head width W4. In some embodiments the first head width W3 is greater than the second head width W4. In other embodiments the first head width W3 is less than the second head width W4. In some embodiments the first head width W3 can be in the range of 4 mm to 12 mm, among other ranges that are suitable and contemplated herein. In some embodiments the width first head width W3 can be 6 mm. In some embodiments the first head width W3 is greater than 6 mm, and in other embodiments the first head width W3 is less than 6 mm. In some embodiments the second head width W4 can be in the range of 4 mm to 12 mm, among other ranges that are suitable and contemplated herein. In some embodiments the second head width W4 can be 6 mm. In some embodiments the second head width W4 is greater than 6 mm, and in other embodiments the second head width W4 is less than 6 mm.

In various embodiments the head 214 can comprise a first end member 206 at the first end 216 and a middle member 210 coupled to, or integral with, the first end member 206. The first end member 206 and the middle member 210 can be of any shape and/or size suitable to perform an osteotomy, such as, a wedge-shaped osteotomy, straight-cut osteotomy, and/or parallel-cut osteotomy. The head 214 can further include a cut guide first side 202 and a cut guide second side 204.

In various embodiments, the head 214 can include a second end member 208 at the second end 218. The middle member 210 can be coupled to or integral with the second end member 208. The middle member 210 can have a first width W5 proximal to the first end member 206 and a second width W6 that is proximal to the second end member 208. In some embodiments the first width W5 can be the same as the second width W6. In other embodiments the first width W5 is greater than the second width W6. In other embodiments the first width W5 is less than the second width W6. The first width W5 can be less than or equal to the first head width W3. The second width W6 can be less than or equal to the second head width W4.

The middle member 210 can have one or more slot(s) 230 formed through it. The one or more slots can be parallel or angled relative to each other. At least one slot 230 can be perpendicular relative to the first end member 206 (e.g., see FIGS. 2F, 2G, 2H, 2I, 2J), or it can be angled relative to the first end member (e.g., see FIGS. 2K, 2L, 2M). The slot(s) 230 can be of any suitable shape and/or size to receive a cutting instrument 1008 (FIG. 10E) suitable to perform an osteotomy, such as, a wedge-shaped osteotomy, straight-cut osteotomy, and/or parallel-cut osteotomy. The cutting instrument 1008 can be at least one of any instrument and/or device capable of cutting bone, such as, a blade, a saw blade, double sided blade, a rasp, an osteotome, etc., among other instruments and/or devices that are possible and contemplated herein.

The cut guide 200 can include at least one placement device 240. The placement device 240 can comprise at least one of a handle, a handlebar, a magnet, a bar, a knob, a hold, a grip, a shaft, a tab, a ring, a pull, among other devices that are possible and contemplated herein. The placement device 240 can be coupled to any portion of the cut guide 200. In various embodiments the placement device 240 can be coupled to at least one of the first end 216, the second end 218, the middle member 210, among other locations that are possible and contemplated herein. In some embodiments the cut guide 200 can include at least two placement devices 240. The placement device 240 can include an attachment mechanism 242. The placement device 240 attachment mechanism 242 can include at least one of a platform, a handle, an aperture, a slot, a clamp, a pin, a k-wire, an olive wire, a blade, and/or a detent, among other devices that are possible and contemplated herein. In the pictured embodiment the placement device attachment mechanism 242 is a slot configured to receive a k-wire. The cut guide 200 can include a securing device 244 (e.g., see FIG. 2N). The securing device 244 can include any device capable of securing at least a portion of the cut guide 200 to at least a portion of the frame 100 and can include at least one of a post, an extension, an aperture, a ball bearing, a spring, a recess, a detent, a snap, a tongue, a groove, a screw, a pin, a magnet, a notch, and/or a bore, among other devices that are possible and contemplated herein. The securing device 244 can have a complimentary securing device 128, and/or shape, and/or recess, etc., on at least a portion of the frame 100, such as at least a portion of the first section 102, the second section 104, the third section 106, the fourth section 108, and/or the attachment mechanism 112, among other portions of the frame that are possible, each of which is contemplated herein. In at least one pictured embodiment the securing device 244 is coupled to the head 214 and shaped to conform to the frame top 120 such that the cut guide 200 and securing device 244 form an interference fit with the frame 100, keeping the head 214 securely in place within the window 110. In at least one embodiment the radiograph positioning tool 114 is also at least one complimentary securing device 128 (e.g., see FIG. 3C).

In at least one embodiment the surgical system 10 and/or the cut guide 200 can comprises at least two securing devices 244. The cut guide 200 can comprise a first securing device 244a which can be an aperture. The surgical system 10 and/or cut guide can comprise a second securing device 244b which can be a screw. In at least one embodiment the frame 100 can comprise at least one complimentary securing device 128, which can be an aperture. (e.g., see FIG. 3E).

Turning now to FIGS. 3A through 3E. In various embodiments the first head width W3 and the second head width W4 are slightly less than the first window width W1 and the second window width W2 respectively, such that the head 214 can fit within the window 110. In some embodiments, the head 214 can fit within the window 110 and make contact with at least a portion of at least one of the first section 102, the second section 104, the third section 106, and the fourth section 108. The head bottom 302 can be flat, shaped similar to the frame bottom 122, and/or configured to conform to at least one bone, among other shapes and/or configurations that are possible, each of which is contemplated herein.

Figure 4B:
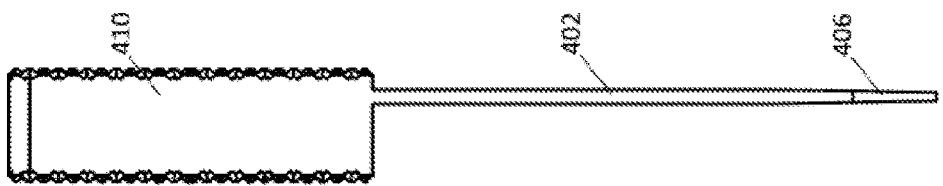
FIGS. 4A through 4C are schematic diagrams illustrating various embodiments of the surgical system including an aligner.
Figure 4A:
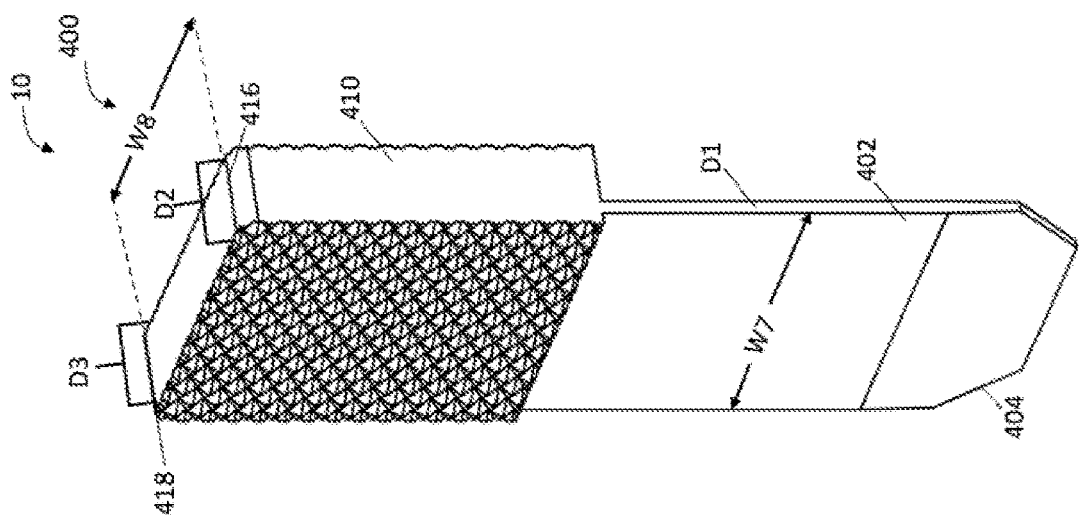
Figure 3E:
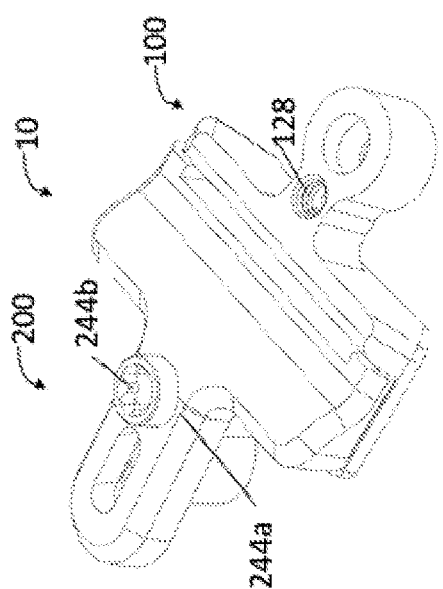
Figure 4C:
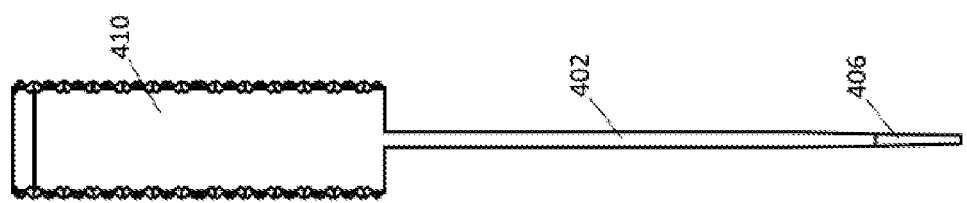

Referring to FIGS. 4A through 4C. The surgical system 10 can include an aligner 400. The aligner 400 can include a shim 402. The shim 402 can have any size and/or shape suitable to assist in performing an osteotomy, such as, a wedge-shaped osteotomy, straight-cut osteotomy, and/or parallel-cut osteotomy. The shim 402 can have a shim width W7. The shim width can be uniform, tapered (404), and/or curved, among other shapes that are possible and contemplated herein. The shim can have a shim depth D1 which can be uniform, and/or tapered (406), among other shapes that are possible and contemplated herein.

The aligner 400 can include a grip 410 with a grip width W8, a first grip depth D2 at a first grip end 416 and a second grip depth D3 at a second grip end 418. In some embodiments the shim width W7 is equal to the grip width W8. In some embodiments the shim width W7 is greater than that grip width W8. In other embodiments the shim width W7 is less than the grip width W8. In various embodiments the first grip depth D2 can be the same as the second grip depth D3 such that the grip depth is uniform. In other embodiments the first grip depth D2 can be different from the second grip depth D3. In some embodiments this difference between D2 and D3 is such that the grip depth tapers. In some embodiments the first grip depth D2 can be greater than the second grip depth D3. In other embodiments the first grip depth D2 can be less than the second grip depth D3. At least a portion of the grip 410 surface can be high friction, or have a high friction coating, such as, knurling, grooves, titanium coating, stippling, among other surfaces that are possible and contemplated herein.

The shim 402 can be centered on or off-center from the first grip depth D2. The shim 402 can be centered on or off-center from the second grip depth D3. The shim 402 can be centered on (e.g., see FIG. 4C) or off-center (e.g., see FIG. 4B) from both the first grip depth D2 and the second grip depth D3.

Figure 5B:
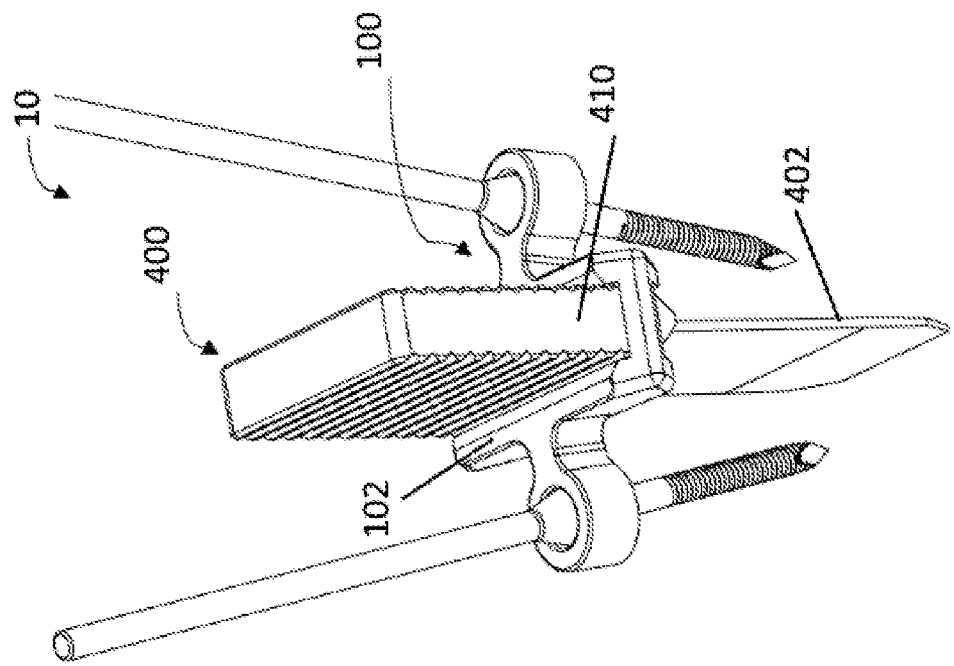
FIGS. 5A and 5B are schematic diagrams illustrating various embodiments of the surgical system including the aligner inserted into various embodiments of the frame.
Figure 5A:
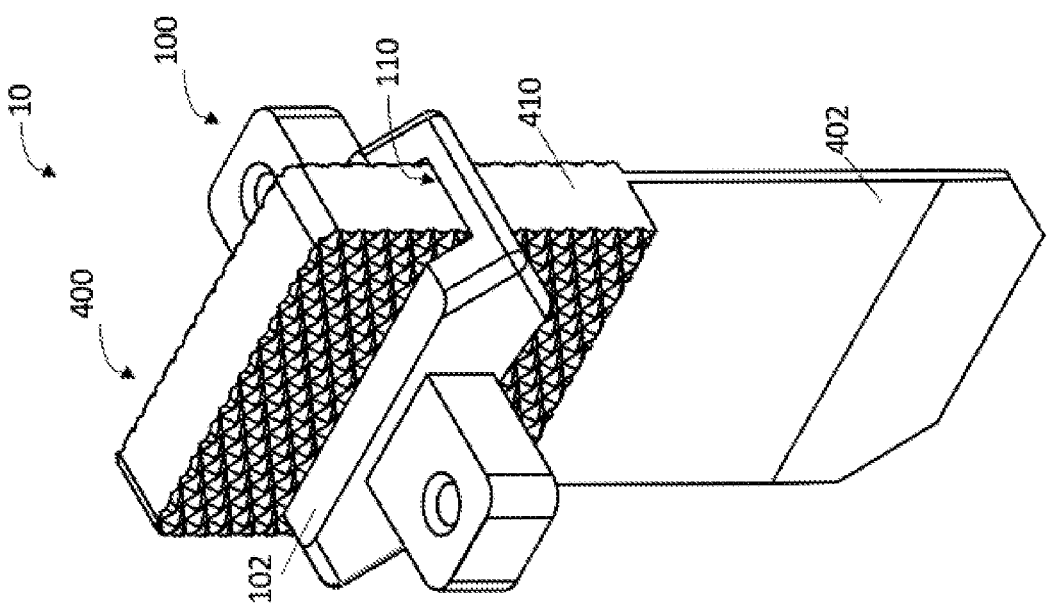

Referring now to FIGS. 5A and 5B. At least a portion of the aligner 400 can be a similar size and shape as the window 110. In various embodiments the grip 410 is a smaller size and/or shape as the window 110 such that the grip 410 can fit within the window 110 and contact at least a portion of the first section 102, the second section 104, the third section 106 and the fourth section 108. In various embodiments the first grip depth D2 is less than the first window width W1 and the second grip depth D3 is less than the second window width W2 such that the grip 410 can fit within the window 110 and contact at least a portion of the first section 102, the second section 104, the third section 106 and the fourth section 108.

In additional or alternative embodiments, the aligner 400 can be coupled to, or integral with frame 100 (e.g., see FIGS. 6A and 6B). In additional or alternative embodiments, the aligner 400 can be coupled to, or integral with, the cut guide 200.

Referring now to FIGS. 7A through 7C, at least in the illustrated embodiment, surgical system 10 is comprised of the frame 100 (e.g., see FIG. 7A), the cut block 200 (e.g., see FIG. 7C), and the aligner 400 (e.g., see FIG. 7B). The window 110, the head 214, and at least a portion of the grip 410 are complimentary in size and shape. In the pictured embodiment they each taper from the second end (118, 218, and 418 respectively) to the first end (116, 216, and 416 respectively). The cut block 200 is a complimentary size and/or shape to the window 110 such that the head 214 can fit within the window. In some embodiments the head 214 can make contact with at least a portion of the first side 102, the second side 104, the third side 106, and the fourth side 108 (e.g., see FIG. 7E). The aligner 400 is a similar size and/or shape to the window 110. In some embodiments the grip 410 can fit within the window and make contact with the first side 102, the second side 104, the third side 106, and the fourth side 108 (e.g., see FIG. 7D).

Referring now to FIGS. 8A through 9D. In various embodiments the first section 102 can have a frame first side 802 and the second section 104 can have a frame second side 804. The frame first side 802 can be parallel with the frame second side 804 (e.g., see FIGS. 8A and 8B). The frame first side 802 can be angled relative to the frame second side 804 (e.g., see FIGS. 8C, 8D, 9B, 9C, and 9D). The frame first side 802 can be perpendicular to the frame top 120a of the first section 102 (e.g., see FIG. 8A), or it can be angled relative to the frame top 120a of the first section 102 (e.g., see FIGS. 8B, 8C, 8D, 8E, 9B, 9C, and 9D). The frame second side 804 can be perpendicular to the frame top 120b of the second section 104 (e.g., see FIG. 8A), or it can be angled relative to the frame top 120b of the second section 104. Similarly, in various embodiments, the cut guide first side 202 can be parallel with the cut guide second side 204 (e.g., see FIG. 8E). The cut guide first side 202 can be angled relative to the cut guide second side 204 (e.g., see FIGS. 8F and 8G). The cut guide first side 202 can be perpendicular to a top 820 of the cut guide 200 head 214 (e.g., see FIG. 2A), or it can be angled relative to the top 820 of the head 214 (e.g., see FIGS. 8E, 8F, and 8G). The cut guide second side 204 can be perpendicular to the top 820 of the head 214 (e.g., see FIG. 2A), or it can be angled relative to the top 820 of the head 214 (e.g., see FIGS. 8E, 8F, and 8G).

In various embodiments the frame 100 can include a securing device 128, such as a notch 902 on at least one of the first section 102, the second section 104, the third section 106, and/or the fourth section 108. In some embodiments the frame 100 includes two notches with a notch length L2 between them. The aligner 400 and/or cut guide 200 can include at least one securing device 242 and/or at least one securing mechanism 244, such as complimentary bumps(s) (to fit within the notch(es) 902), or the aligner 400 and/or cut guide 200 can be shaped to fit within the notches 902 (e.g., see FIG. 9C through 9D).

In the following examples, the first bone 1002 is cut during the method steps. This is for simplicity and ease of explanation. The first bone 1002 can be cut prior to the listed steps. This prior cut could be instead of, or in addition to, the cut during the method steps.

Figure 11A:
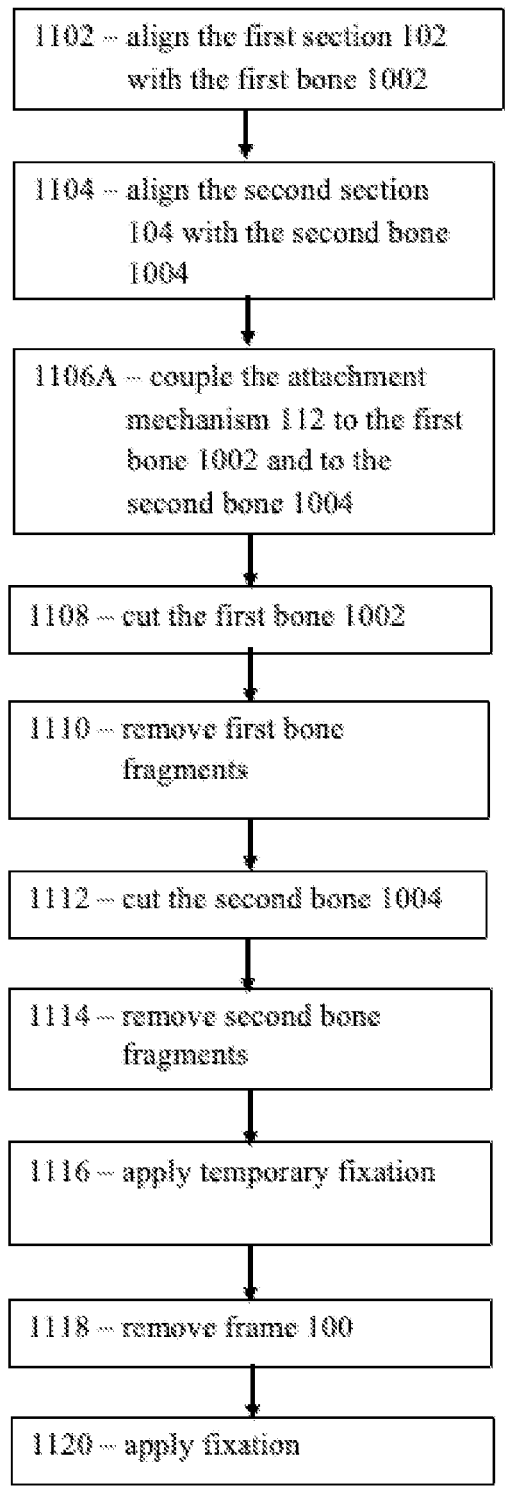
FIGS. 11A and 11B are flow charts that illustrate embodiments of performing an osteotomy with the frame.

FIG. 11A is a flow chart diagram illustrating one embodiment of a method 1100A for performing a wedge-shaped osteotomy, straight-cut osteotomy, and/or parallel-cut osteotomy.

At least in the illustrated embodiment, the method 1100A can include aligning the first section 102 of the frame 100 over a first bone 1002 (block 1102).

In at least one embodiment, the second bone 1004 can be aligned with the second section 104 of the frame 100 (block 1104).

In some embodiments, the frame 100 can be coupled to the first bone 1002 by coupling the attachment mechanism 112 to the first bone 1002 (block 1106A). The frame 100 can be coupled to the second bone 1004 by coupling the attachment mechanism 112 to the second bone 1004 (e.g., see FIG. 10C).

In the illustrated embodiment, the alignment of the first bone 1002 with the first section 102 can be checked and the alignment of the second bone 1004 with the second section 104 can be checked (block 1107). In one embodiment the alignment of the first bone 102 with the first section 1002, and the alignment of the second bone 1004 with the second section can be checked by placing the first bone 1002 and the second bone 1004 under fluoroscopy with an anteroposterior (AP) view. The radiograph positioning tool 114 can be used to make sure the fluoroscopy instrument is positioned correctly. The alignment of the first bone 1002 with the first section 102 and the alignment of the second bone 1004 with the second section 104 can be checked before or after the first section 102 is coupled to the first bone 102 and the second section 104 is coupled to the second bone 1004.

In at least one embodiment, the radiograph positioning tool 114 can be an aperture. The fluoroscopy instrument is positioned correctly when the full shape of the aperture appears in the radiograph. For example, in one embodiment the positioning tool 114 is a circular aperture. In this embodiment, the fluoroscopy instrument is not positioned correctly if a half-circle, or any other shape except for a full circle appears in the radiograph. The shape of the aperture would appear lighter than the frame 100 in the radiograph.

In other embodiments, the radiograph positioning tool 114 can be a fin, post, or extension. The fluoroscopy instrument is positioned correctly when only the top view shape of the fin or extension appears in the radiograph. For example, in one embodiment the positioning tool 114 is a cylindrical rod. In this embodiment, the fluoroscopy instrument is not positioned correctly if a rectangular shape, or any other shape except for a full circle appears in the radiograph. The circular end-shape of the rod would appear darker than the frame 100 in the radiograph.

In various embodiments, the radiograph positioning tool 114 can be two bars, one on the frame top 120 and one on the frame bottom 122. The fluoroscopy instrument is positioned correctly when only one bar appears in the radiograph.

In some embodiments, the first bone 1002 can be cut by any cutting means (block 1108). The first bone 1002 can be cut with a cutting instrument 1008 (e.g., see FIG. 10E). At least a portion of the cutting instrument 1008 can be held against the frame first side 802 to assist in keeping the cutting instrument 1008 straight and keep the cutting instrument 1008 from jumping or skiving and damaging the tissue surrounding the osteotomy site.

In certain embodiments, bone fragments from the first bone 1002 can be removed from the osteotomy site (block 1110). The bone fragments from the first bone 1002 can be removed in any suitable manner. In some embodiments, the bone fragments from the first bone 1002 can be removed through the window 110.

In some embodiments, the second bone 1004 can be cut by any cutting means (block 1112). In various embodiments, the second bone 1004 can be cut with the cutting instrument 1008. At least a portion of the cutting instrument 1008 can be held against the frame second side 804 to assist in keeping the cutting instrument 1008 straight and keep the cutting instrument 1008 from jumping or skiving and damaging the tissue surrounding the osteotomy site.

In certain embodiments, bone fragments from the second bone 1004 can be removed (block 1114). The bone fragments from the second bone 1004 can be removed in any suitable manner. In some embodiments the bone fragments from the second bone 1004 can be removed through the window 110.

At least in the illustrated embodiment, the first bone 1002 and the second bone 1004 can be compressed together and temporary fixation applied (block 1116). Temporary fixation can be any means that will keep the bones in place while their position is checked. Temporary fixation can be the placement of K-wires, olive pins, external fixation, etc., among other means possible, each of which is contemplated herein.

In certain embodiments, the bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible, each of which is contemplated herein.

In some embodiments, the frame 100 can be removed (block 1118). In certain embodiments the frame 100 can be removed after checking bone positions. In other embodiments the frame 100 can be removed before checking bone positions.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

At least in the illustrated embodiment, fixation can be applied (block 1120). Applying fixation can include applying at least one fixation device 1010 which can be anything capable of securing the bones such as, a bone plate, an intramedullary device, an intramedullary nail, a bone screw, a staple, external fixation, etc., among other fixation devices that are possible, each of which is contemplated herein. The at least one fixation device 1010 can be applied to the first bone 1002 and/or to the second bone 1004.

Figure 10A:
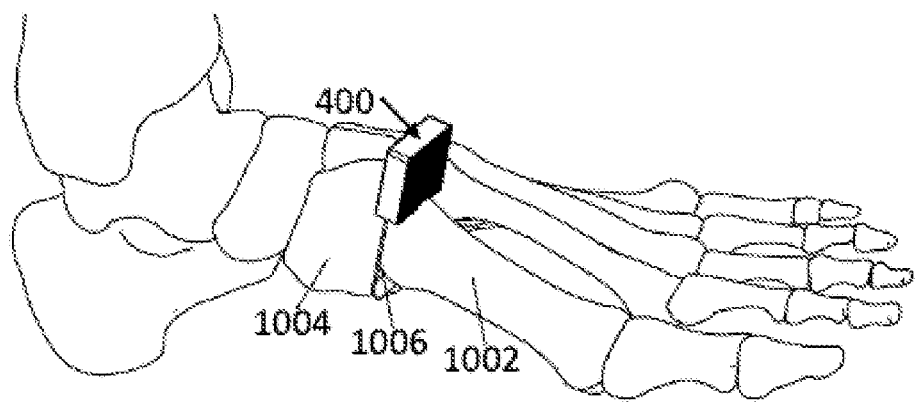
FIGS. 10A through 10G are schematic diagrams illustrating various embodiments of the surgical system.
Figure 10B:
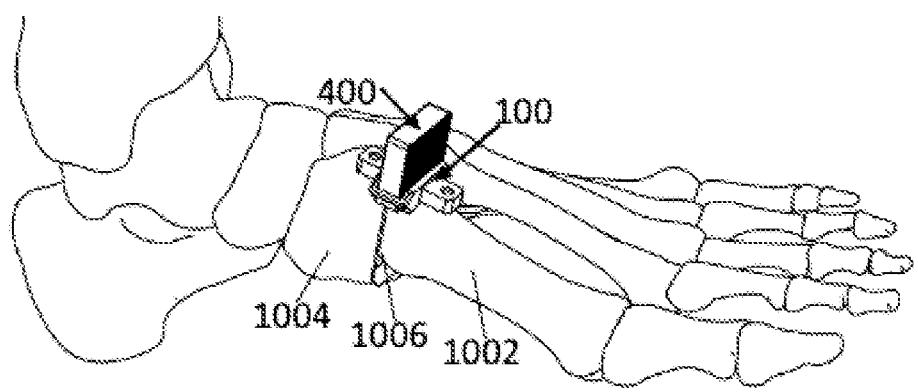
Figure 10C:
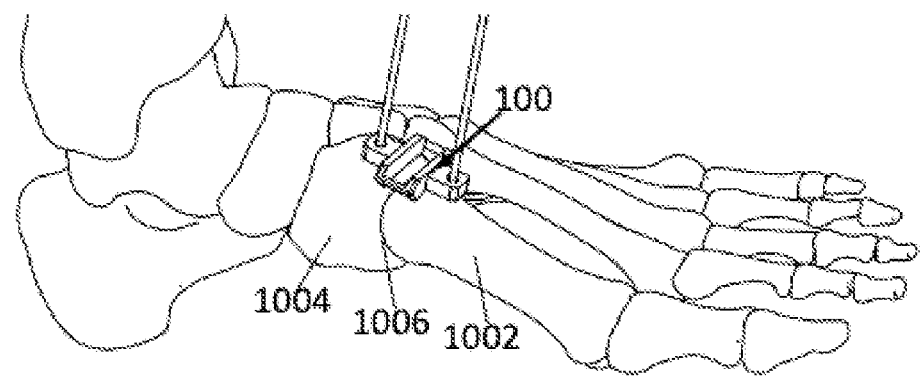
Figure 10D:
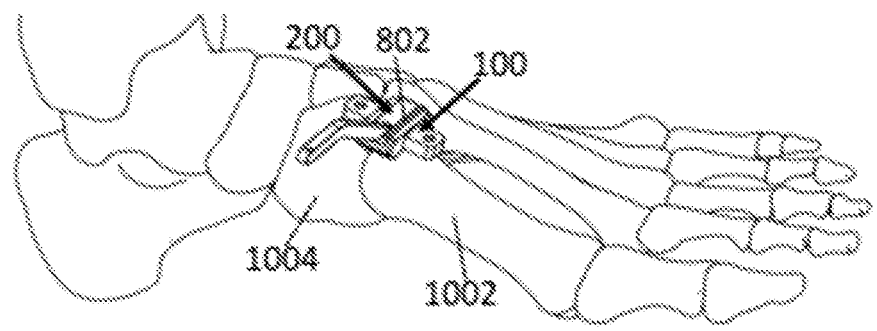
Figure 10E:
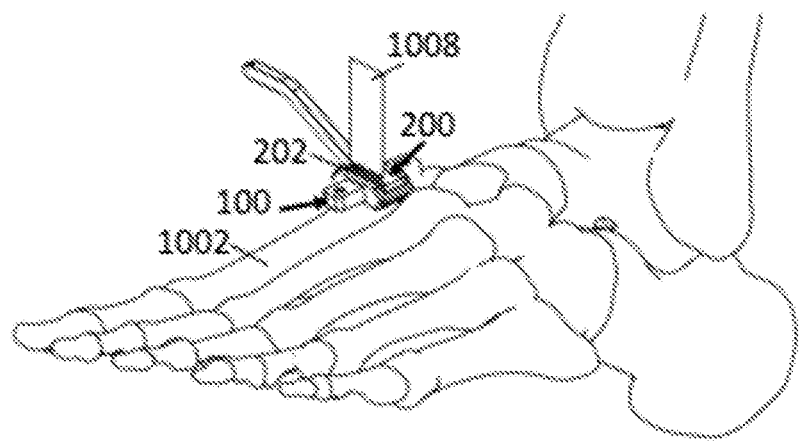
Figure 11B:
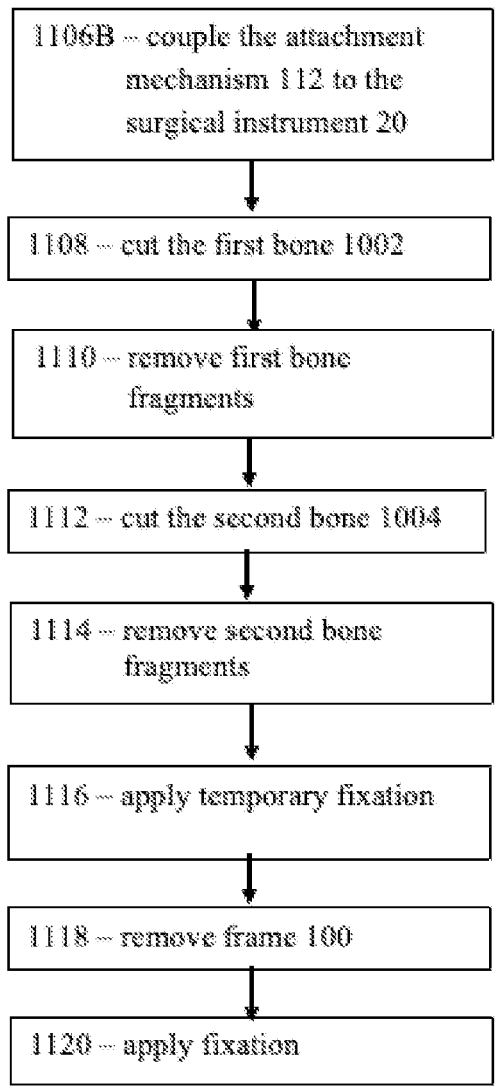

FIG. 11B is a flow chart diagram illustrating one embodiment of a method 1100B for performing an osteotomy. At least in the illustrated embodiment, the method 1100B can include coupling the attachment mechanism 112 of the frame 100 to a surgical instrument 20 (block 1106B) (e.g. see FIG. 1F). In some embodiments, the first bone 1002 can be cut with the cutting instrument 1008 (block 1108) (e.g., see FIG. 10E). The cutting instrument 1008 can be held against the frame first side 802 to assist in keeping the blade straight and to keep the cutting instrument from jumping or skiving and damaging bone and/or tissue near the osteotomy site.

In certain embodiments, bone fragments from the first bone 1002 can be removed from the osteotomy site (block 1110). The bone fragments from the first bone 1002 can be removed in any suitable manner. In some embodiments, the bone fragments from the first bone 1002 can be removed through the window 110.

In some embodiments, the second bone 1004 can be cut with the cutting instrument 1008 (block 1112). In certain embodiments, bone fragments from the second bone 1004 can be removed (block 1114). The bone fragments from the second bone 1004 can be removed in any suitable manner. In some embodiments the bone fragments from the second bone 1004 can be removed through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

At least in the illustrated embodiment, the first bone 1002 and the second bone 1004 can be compressed together and temporary fixation applied (block 1116). Temporary fixation can be any means that will keep the bones in place while their position is checked. Temporary fixation can be the placement of K-wires, olive pins, external fixation, locking of the surgical instrument 20, etc., among other means possible, each of which is contemplated herein.

In certain embodiments, the bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible, each of which is contemplated herein.

In some embodiments, the frame 100 can be removed (block 1118). In certain embodiments the frame 100 can be removed after checking bone positions. In other embodiments the frame 100 can be removed before checking bone positions.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

At least in the illustrated embodiment, fixation can be applied (block 1120). Applying fixation can include applying at least one fixation device 1010 which can be anything capable of securing the bones such as, a bone plate, an intramedullary device, an intramedullary nail, a bone screw, a staple, external fixation, etc., among other fixation devices that are possible, each of which is contemplated herein. The at least one fixation device 1010 can be applied to the first bone 1002 and/or to the second bone 1004.

Figure 12A:
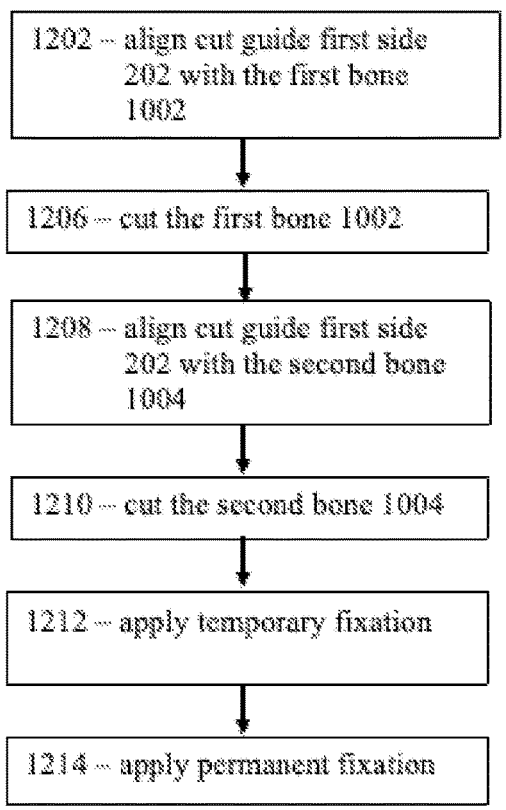
FIGS. 12A and 12B are flow charts illustrating embodiments of performing an osteotomy with the cut guide.

FIG. 12A is a flow chart diagram illustrating one embodiment of a method 1200A for performing a wedge-shaped osteotomy, straight-cut osteotomy, and/or parallel-cut osteotomy.

At least in the illustrated embodiment, the method 1200A can include aligning the cut guide first side 202 with the first bone 1002. The first bone 1002 can be cut with the cutting instrument 1008 (block 1206). At least a portion of the cutting instrument 1008 can be held against the cut guide first side 202 to assist in keeping the cutting instrument 1008 straight and keep the cutting instrument 1008 from jumping or skiving and damaging bone and/or tissue near the osteotomy site. If desired, bone fragments from the first bone 1002 can be removed from the osteotomy site in any suitable manner.

The cut guide 200 can be removed, reversed, and replaced, aligning the cut guide first side 202 with the second bone 1004. The second bone 1004 can be cut with the cutting instrument 1008 (block 1210). At least a portion of the cutting instrument 1008 can be held against the cut guide first side 202 to assist in keeping the cutting instrument 1008 straight and to keep the cutting instrument 1008 from jumping or skiving and damaging bone and/or tissue near the osteotomy site. If desired, bone fragments from the second bone 1004 can be removed.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

At least in the illustrated embodiment, the first bone 1002 and the second bone 1004 can be compressed together and temporary fixation applied (block 1212). Temporary fixation can be any means that will keep the bones in place while their position is checked. Temporary fixation can be the placement of K-wires, olive pins, external fixation, locking of the surgical instrument 20, etc., among other means possible, each of which is contemplated herein.

In certain embodiments, the bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible, each of which is contemplated herein.

At least in the illustrated embodiment, fixation can be applied (block 1214). Applying fixation can include applying at least one fixation device 1010 which can be anything capable of securing the bones such as, a bone plate, an intramedullary device, an intramedullary nail, a bone screw, a staple, external fixation, etc., among other fixation devices that are possible, each of which is contemplated herein. The at least one fixation device 1010 can be applied to the first bone 1002 and/or to the second bone 1004.

Figure 12B:
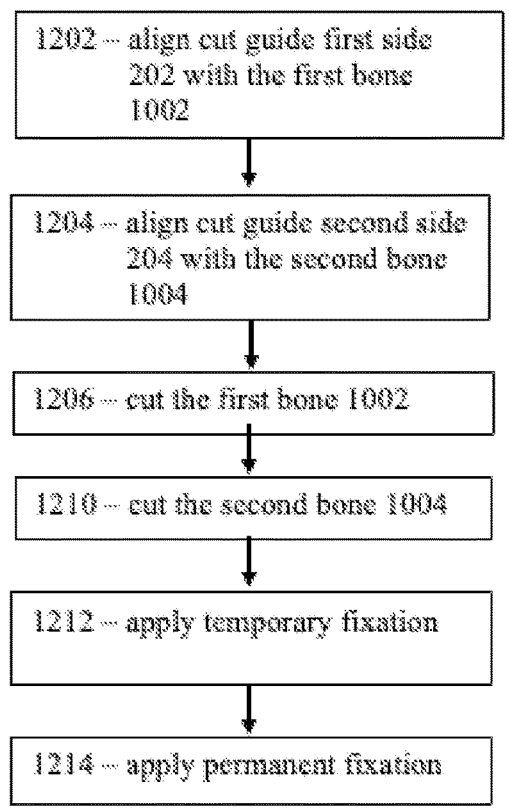

FIG. 12B is a flow chart diagram illustrating one embodiment of a method 1200B for performing a wedge-shaped osteotomy, straight-cut osteotomy, and/or parallel-cut osteotomy. At least in the illustrated embodiment, the method 1200B can include aligning the cut guide first side 202 with the first bone 1002 (block 1202). The first bone 1002 can be cut with the cutting instrument 1008 (block 1206). At least a portion of the cutting instrument 1008 can be held against the cut guide first side 202 to assist in keeping the cutting instrument straight and to keep the cutting instrument 1008 from jumping or skiving and damaging bone and/or tissue near the osteotomy site. If desired, bone fragments from the first bone 1002 can be removed from the osteotomy site.

In some embodiments, the second bone 1004 can be cut with the cutting instrument 1008 (block 1210). At least a portion of the cutting instrument 1008 can be held against the cut guide second side 204 to assist in keeping the cutting instrument 1008 straight and to keep the cutting instrument 1008 from jumping or skiving and damaging bone and/or tissue near the osteotomy site. If desired, bone fragments from the second bone 1004 can be removed.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

At least in the illustrated embodiment, the first bone 1002 and the second bone 1004 can be compressed together and temporary fixation applied (block 1212). Temporary fixation can be any means that will keep the bones in place while their position is checked. Temporary fixation can be the placement of K-wires, olive pins, external fixation, locking of the surgical instrument 20, etc., among other means possible, each of which is contemplated herein.

In certain embodiments, the bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

At least in the illustrated embodiment, the bones 1002 and 1004 can be fixed by applying at least one fixation device 1010 (block 1214) which can be anything capable of securing the bones such as, a bone plate, an intramedullary device, an intramedullary nail, a bone screw, a staple, external fixation, etc., among other fixation devices that are possible, each of which is contemplated herein. The at least one fixation device 1010 can be applied to the first bone 1002 and/or to the second bone 1004.

Figure 13A:
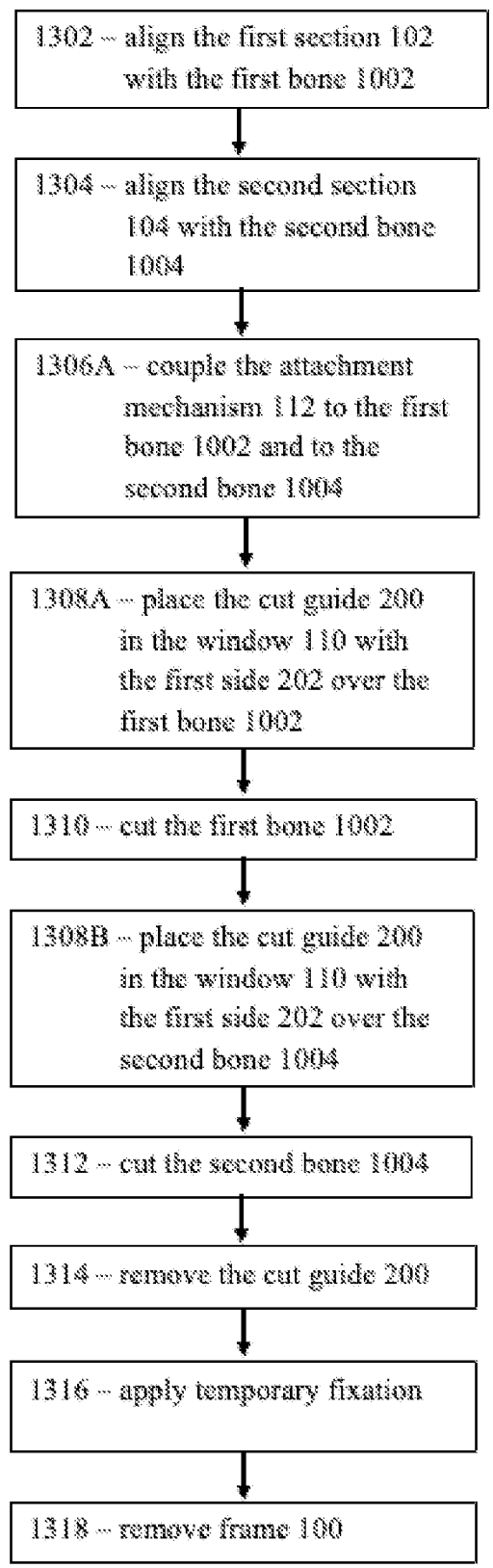
FIGS. 13A through 13C are a flow charts illustrating embodiments of performing an osteotomy with the frame and the cut guide.

FIG. 13A is a flow chart diagram illustrating one embodiment of a method 1300A for performing a wedge-shaped osteotomy, straight-cut osteotomy, and/or parallel-cut osteotomy. At least in the illustrated embodiment, the method 1300A can include aligning the first section 102 of the frame 100 over the first bone 1002 (block 1302). The second bone 1004 can be aligned with the second section 104 of the frame 100 (block 1304). The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Block 1306A) (e.g. see FIG. 10C).

In some embodiments, the cut guide 200 can be placed in the window 110 (block 1308A). The head 214 can be oriented within the frame 100 so that the cut guide first side 202 is over the first bone 1002 (e.g., see FIG. 10D). In certain embodiments the cut guide can be selected from a kit of cut guides.

In at least one embodiment, the first bone 1002 can be cut (block 1310) with the cutting instrument 1008 (e.g., see FIG. 10E). At least a portion of the cutting instrument 1008 can be held against the cut guide first side 202 to assist in keeping it straight and avoid the cutting instrument 1008 jumping or skiving and damaging bone and/or tissue near the osteotomy site.

If desired, bone fragments from the first bone 1002 can be removed from the osteotomy site. The bone fragments can be removed in any suitable manner, such as through the window 110.

Figure 10F:
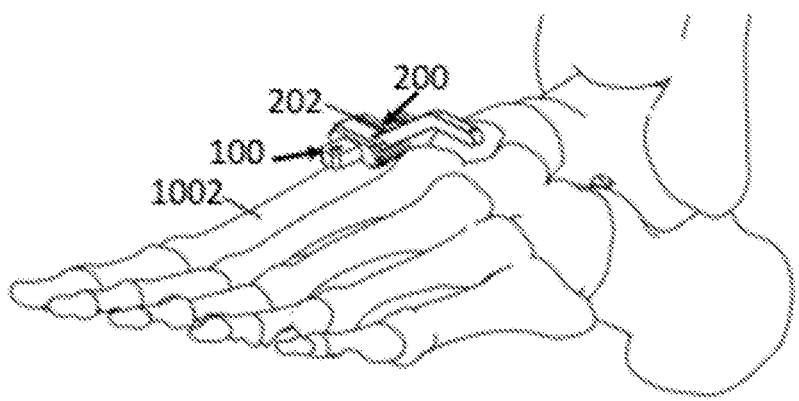

In some embodiments, the cut guide 200 can be removed, reversed, and replaced in the window 110, orienting the cut guide first side 202 over the second bone 1004 (block 1308B) (e.g., see FIG. 10F). In certain embodiments, this can be done without removing the frame 100 which is advantageous because it minimizes time spent on the osteotomy and reduces the risk of misalignment. In alternative or additional embodiments, the cut guide 200 can be removed from the window 110 and replaced (in the window 110) with another cut guide 200 which can be selected from the kit of cut guides 200.

In at least one embodiment, the second bone 1004 can be cut with the cutting instrument 1008 (block 1312). At least a portion of the cutting instrument 1008 can be held against the cut guide first side 202 to assist in keeping the cutting instrument 1008 straight and to keep the cutting instrument 1008 from jumping or skiving and damaging bone and/or tissue near the osteotomy site.

In some embodiments, the cut guide 200 can be removed from the frame 100 (block 1314). If desired, bone fragments from the second bone 1004 can be removed by any suitable means, such as, through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

(Block 1316) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (block 1318). In certain embodiments the frame 100 can be removed after checking bone positions. In other embodiments the frame 100 can be removed before checking bone positions.

Figure 10G:
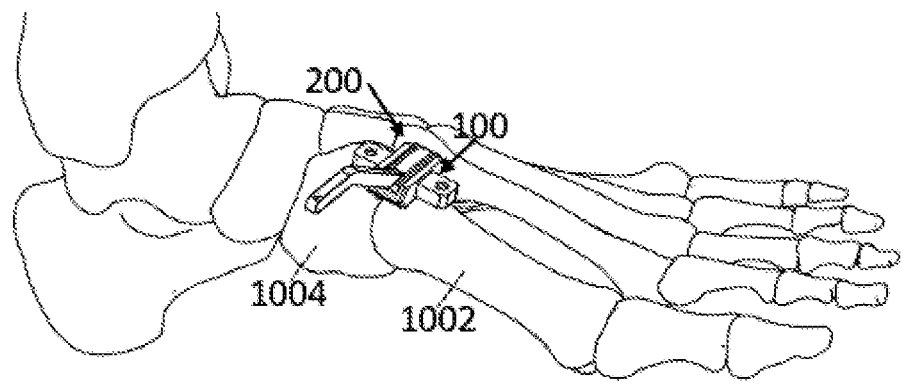
Figure 10H:
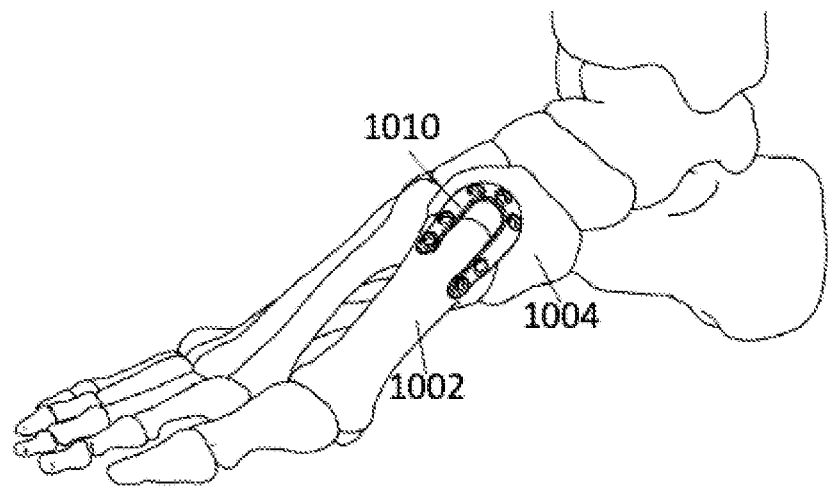
FIG. 10H is a schematic diagram of a fixation device on the foot.

The first bone 1002 and the second bone 1004 can be fixed by coupling the fixation device 1010 to the first bone 1002 and/or the second bone 1004 (e.g., see FIG. 10H).

Figure 13B:
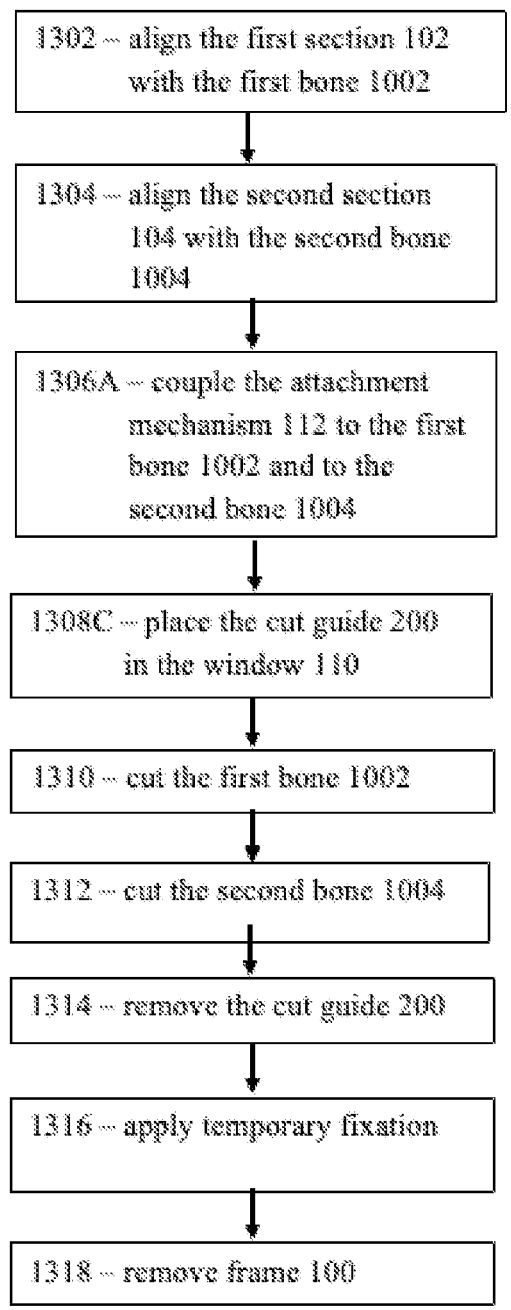

In additional or alternative embodiments, the method of performing an osteotomy (FIG. 13B) can include aligning the first section 102 of the frame 100 over a first bone 1002 (block 1302). The second bone 1004 can be aligned with the second section 104 of the frame 100 (block 1304).

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Block 1306A) (e.g. see FIG. 10C).

The cut guide 200 can be placed in the window 110 (block 1308C) orienting the cut guide first side 202 over the first bone 1002 and the cut guide second side 204 over the second bone 1004 (e.g., see Figure G). In some embodiments the cut guide 200 can be selected from a kit of cut guides 200.

The first bone 1002 can be cut (block 1310) with the cutting instrument 1008. The cutting instrument 1008 can be held against the cut guide first side 202 to assist in keeping the cutting instrument 1008 straight and keep the cutting instrument 1008 from jumping or skiving and damaging bone and/or tissue near the osteotomy site.

If desired, bone fragments from the first bone 1002 can be removed from the osteotomy site. The bone fragments can be removed in any suitable manner, such as through the window 110.

The second bone 1004 can be cut (block 1312). The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (block 1314).

If desired, bone fragments from the second bone 1004 can be removed by any suitable means, such as, through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

(Block 1316). The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the techniques that are possible and contemplated herein.

The frame 100 can be removed (block 1318). In certain embodiments the frame 100 can be removed after checking bone positions. In other embodiments the frame 100 can be removed before checking bone positions.

The first bone 1002 and the second bone 1004 can be fixed by applying the fixation device 1010 to the first bone 1002 and/or the second bone 1004 (e.g., see FIG. 10H).

Figure 13C:
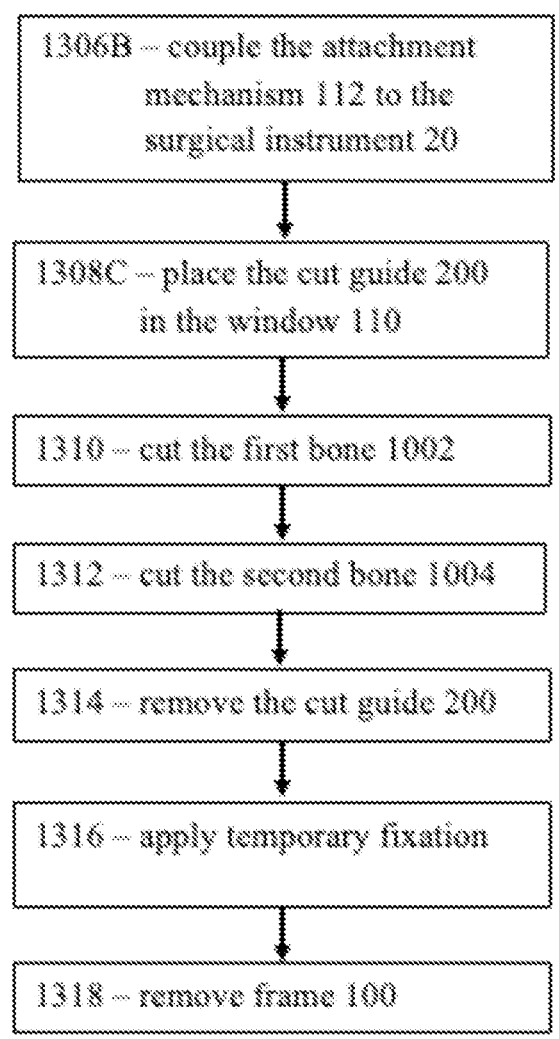

In additional or alternative embodiments, the method of performing an osteotomy (FIG. 13C) can include coupling the attachment mechanism 112 to the surgical instrument 20 (e.g., see FIG. 1F) which places the first section 102 over the first bone 1002 and the second section 104 over the second bone 1004 (block 1306B). The second bone 1004 can be aligned with the second section 104 of the frame 100 (block 1304). The cut guide 200 can be placed in the window 110 (block 1308C), orienting the cut guide first side 202 over the first bone 1002 and the cut guide second side 204 over the second bone 2004 (e.g., see FIG. 10G). In some embodiments the cut guide 200 can be selected from a kit of cut guides 200.

The first bone 1002 can be cut (block 1310) with the cutting instrument 1008. The cutting instrument 1008 can be held against the cut guide first side 202 to assist in keeping the cutting instrument 1008 straight and keep cutting instrument 1008 from jumping or skiving and damaging bone and/or tissue near the osteotomy site.

If desired, the bone fragments from the first bone 1002 can be removed from the osteotomy site. The bone fragments can be removed in any suitable manner, such as through the window 110 by removing and replacing the cut guide 200.

The second bone 1004 can be cut by any cutting means (block 1312). The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (block 1314). If desired, bone fragments from the second bone 1004 can be removed by any suitable means, such as, through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

(block 1316) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the techniques that are possible and contemplated herein.

The frame 100 can be removed (block 1318). In certain embodiments the frame 100 can be removed after checking bone positions. In other embodiments the frame 100 can be removed before checking bone positions.

The bones 1002 and 1004 can be fixed by applying at least one fixation device 1010. The at least one fixation device 1010 can be applied to the first bone 1002 and applied to the second bone 1004 (e.g., see FIG. 10H).

In additional or alternative embodiments, the method of performing an osteotomy (FIG. 14A) can include placing the aligner 400 in the target joint 1006 (block 1402) (e.g., see FIG. 10A). The target joint 1006 can be the space between the first bone 1002 and the second bone 1004. When the first bone 1002 and the second bone 1004 are different bones, the target joint 1006 is the joint between them. When the first bone 1002 and the second bone 1004 are different portions of the same bone, then the target joint 1006 is the space where the two bone portions meet, for example, the space can be a fracture site or osteotomy site. The aligner 400 can be placed in the target joint 1006 by placing the shim 402 in the target joint 1006.

The frame 100 can be positioned over the target joint 1006 by placing it over the aligner 400 (block 1404) (e.g., see FIG. 10B), positioning the first section 102 over the first bone 1002 and the second section 104 over the second bone 1004.

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Block 1406A) (e.g. see FIG. 10C).

(Block 1408) The aligner can be removed by any suitable means, including pulling it up through the window 110.

(Block 1410) The first bone 1002 can be cut by any cutting means. The first bone 1002 can be cut with the cutting instrument 1008. The cutting instrument 1008 can be held against the frame first side 802 to assist in keeping the cutting instrument 1008 straight and avoid the cutting instrument 1008 jumping or skiving and damaging the tissue surround the osteotomy site.

If desired, the bone fragments from the first bone 1002 can be removed from the osteotomy site. The bone fragments can be removed in any suitable manner. In some embodiments the bone fragments can be removed through the window 110.

(Block 1412) The second bone 1004 can be cut by any cutting means. The second bone 1004 can be cut with the cutting instrument 1008. The cutting instrument 1008 can be held against the frame second side 804 to assist in keeping the cutting instrument 1008 straight and avoid the cutting instrument 1008 jumping or skiving and damaging the tissue surround the osteotomy site.

If desired, the bone fragments from the second bone 1004 can be removed. The bone fragments can be removed in any suitable manner. In some embodiments the bone fragments can be removed through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

(Block 1416) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (block 1418). In certain embodiments the frame 100 can be removed after checking bone positions. In other embodiments the frame 100 can be removed before checking bone positions.

The bones 1002 and 1004 can be fixed by applying at least one fixation device 1010 (block 1214). The at least one fixation device 1010 can be applied to the first bone 1002 and/or applied to the second bone 1004 (e.g., see FIG. 10H).

In additional or alternative embodiments, the method of performing an osteotomy (FIG. 14B) can include placing the aligner 400 in a target joint 1006 (block 1402) (e.g., see FIG. 10A). In various embodiments the aligner 400 can be placed in the target joint 1006 by placing the shim 402 in the target joint 1006.

In the pictured embodiment, the frame 100 can be positioned over the target joint 1006 by placing it over the aligner 400 (block 1404) (e.g., see FIG. 10B), positioning the first section 102 over the first bone 1002 and the second section 104 over the second bone 1004.

In the pictured embodiment, the frame 100 can be coupled to the surgical instrument 20 by coupling the attachment mechanism 112 to the surgical instrument 20. (e.g. see FIG. 10C) (Block 1406B).

(Block 1408) The aligner can be removed by any suitable means, including pulling it up through the window 110.

The first bone 1002 can be cut by any cutting means. The first bone 1002 can be cut with the cutting instrument 1008 (Block 1410). The cutting instrument 1008 can be held against the frame first side 802 to assist in keeping the cutting instrument 1008 straight and avoid the cutting instrument 1008 jumping or skiving and damaging the tissue surround the osteotomy site.

If desired, the bone fragments from the first bone 1002 can be removed from the osteotomy site. The bone fragments can be removed in any suitable manner. In some embodiments the bone fragments can be removed through the window 110.

(Block 1412) The second bone 1004 can be cut by any cutting means. The second bone 1004 can be cut with the cutting instrument 1008. The cutting instrument 1008 can be held against the frame second side 804 to assist in keeping the cutting instrument 1008 straight and avoid the cutting instrument 1008 jumping or skiving and damaging the tissue surround the osteotomy site.

If desired, the bone fragments from the second bone 1004 can be removed. The bone fragments can be removed in any suitable manner. In some embodiments the bone fragments can be removed through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

(Block 1416) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The bones 1002 and 1004 can be fixed by applying at least one fixation device 1010 (Block 1418). The at least one fixation device 1010 can be applied to the first bone 1002 and/or applied to the second bone 1004 (e.g., see FIG. 10H).

Figure 15A:
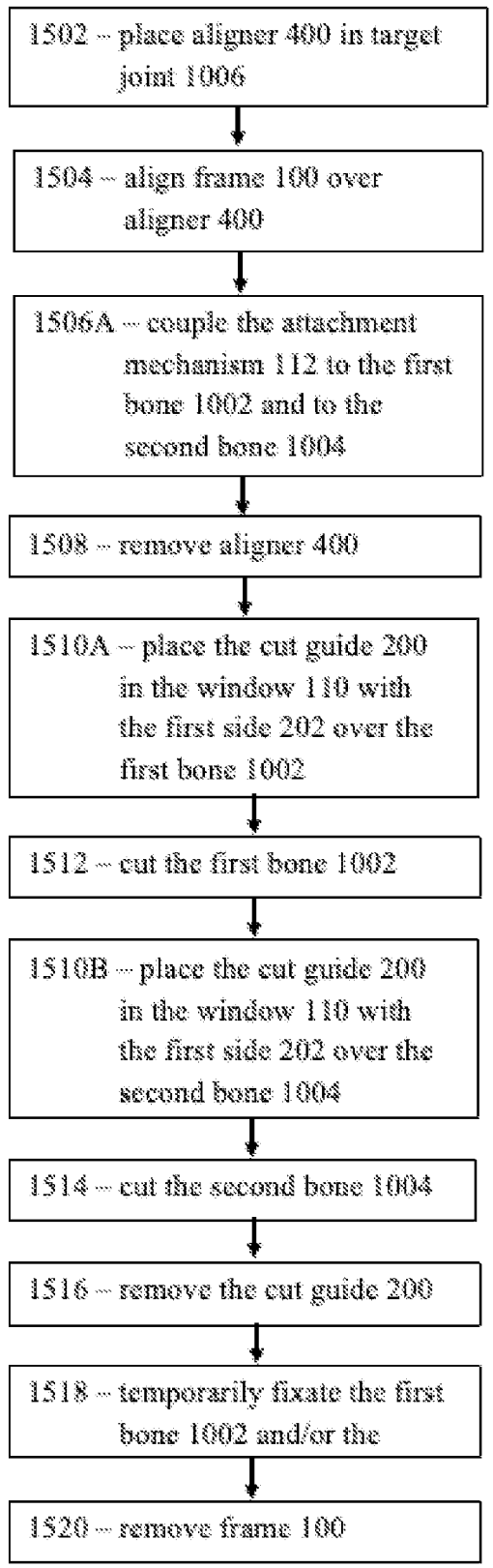
FIGS. 15A and 15B are flow charts illustrating embodiments of performing an osteotomy with the frame, the cut guide, and the aligner.

In additional or alternative embodiments, the method of performing an osteotomy (FIG. 15A) can include placing the aligner 400 in a target joint 1006 (block 1502) (e.g., see FIG. 10A). In the pictured embodiment, the aligner 400 can be placed in the target joint 1006 by placing the shim 402 in the target joint 1006. The frame 100 can be positioned over the target joint 1006 by placing it over the aligner 400 (block 1504) (e.g., see FIG. 10B), positioning the first section 102 over the first bone 1002 and the second section 104 over the second bone 1004.

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Block 1506A) (e.g. see FIG. 10C).

(Block 1508) The aligner can be removed by any suitable means, including pulling it up through the window 110.

(Block 1510A) The cut guide 200 can be placed in the window 110 orienting the cut guide first side 202 over the first bone 1002 (e.g., see FIGS. 10D and 10E). In some embodiments the cut guide 200 can be selected from a kit of cut guides 200.

The first bone 1002 can be cut (block 1512) with the cutting instrument 1008. The cutting instrument 1008 can be held against the cut guide first side 202 to assist in keeping it straight and avoid the cutting instrument 1008 jumping or skiving and damaging bone and/or tissue near the osteotomy site.

If desired, the bone fragments from the first bone 1002 can be removed from the osteotomy site. The bone fragments can be removed in any suitable manner, such as through the window 110.

(Block 1510B) The cut guide 200 can be removed, reversed, and replaced orienting the cut guide first side 202 over the second bone 1004 (block 1510B) (e.g., see FIG. 10DF). In some embodiments the cut guide 200 can be replaced with a different cut guide 200 selected from a kit of cut guides 200.

(Block 1514) The second bone 1004 can be cut by any cutting means. The second bone 1004 can be cut with the cutting instrument 1008. The cutting instrument 1008 can be held against the cut guide first side 202 to assist in keeping the cutting instrument 1008 straight and to keep the cutting instrument 1008 from jumping or skiving and damaging bone and/or tissue near the osteotomy site.

The cut guide 200 can be removed from the frame 100 (block 1516). If desired, the bone fragments from the second bone 1004 can be removed by any suitable means, such as, through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

The first bone 1002 and the second bone 1004 can be compressed together and temporary fixation applied (block 1518). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (block 1520). In certain embodiments the frame 100 can be removed after checking bone positions. In other embodiments the frame 100 can be removed before checking bone positions.

The first bone 1002 and the second bone 1004 can be fixed by applying the fixation device 1010 to the first bone 1002 and/or the second bone 1004 (e.g., see FIG. 10H).

Figure 15B:
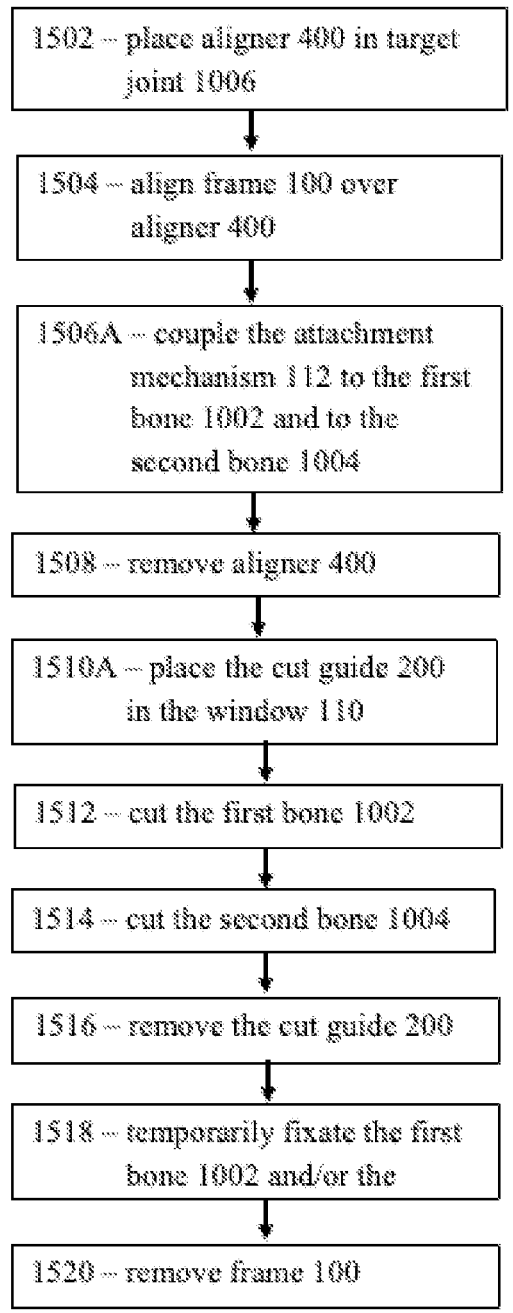

In additional or alternative embodiments, the method of performing an osteotomy (FIG. 15B) can include placing the aligner 400 in a target joint 1006 (block 1502) (e.g., see FIG. 10A). The aligner 400 can be placed in the target joint 1006 by placing the shim 402 in the target joint 1006.

The frame 100 can be positioned over the target joint 1006 by placing it over the aligner 400 (block 1504) (e.g., see FIG. 10B), positioning the first section 102 over the first bone 1002 and the second section 104 over the second bone 1004.

The frame 100 can be coupled to the first bone 1002 by coupling the attachment mechanism 112 to the first bone 1002. The frame 100 can be coupled to the second bone 1004 by coupling the attachment mechanism 112 to the second bone 1004 (block 1506A).

(Block 1508) The aligner can be removed by any suitable means, including pulling it up through the window 110.

(Block 1510A) The cut guide 200 can be placed in the window 110, orienting the cut guide first side 202 over the first bone 1002 and the cut guide second side 204 over the second bone 1004 (e.g., see FIG. 10G). In some embodiments the cut guide 200 can be selected from a kit of cut guides 200.

The first bone 1002 can be cut (block 1512) by any cutting means. The first bone 1002 can be cut with the cutting instrument 1008. The cutting instrument 1008 can be held against the cut guide first side 202 to assist in keeping it straight and avoid the cutting instrument 1008 jumping or skiving and damaging bone and/or tissue near the osteotomy site.

If desired, the cut guide 200 can be removed from the frame 100 and bone fragments from the first bone 1002 can be removed from the osteotomy site. The bone fragments can be removed in any suitable manner, such as through the window 110.

(Block 1514) The second bone 1004 can be cut by any cutting means. The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (block 1516). If desired, the bone fragments from the second bone 1004 can be removed by any suitable means, such as, through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

The first bone 1002 and the second bone 1004 can be compressed together and temporary fixation applied (block 1518). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (block 1520). In certain embodiments the frame 100 can be removed after checking bone positions. In other embodiments the frame 100 can be removed before checking bone positions.

The first bone 1002 and the second bone 1004 can be fixed by applying the fixation device 1010 to the first bone 1002 and/or the second bone 1004 (e.g., see FIG. 10H).

Figure 16C:
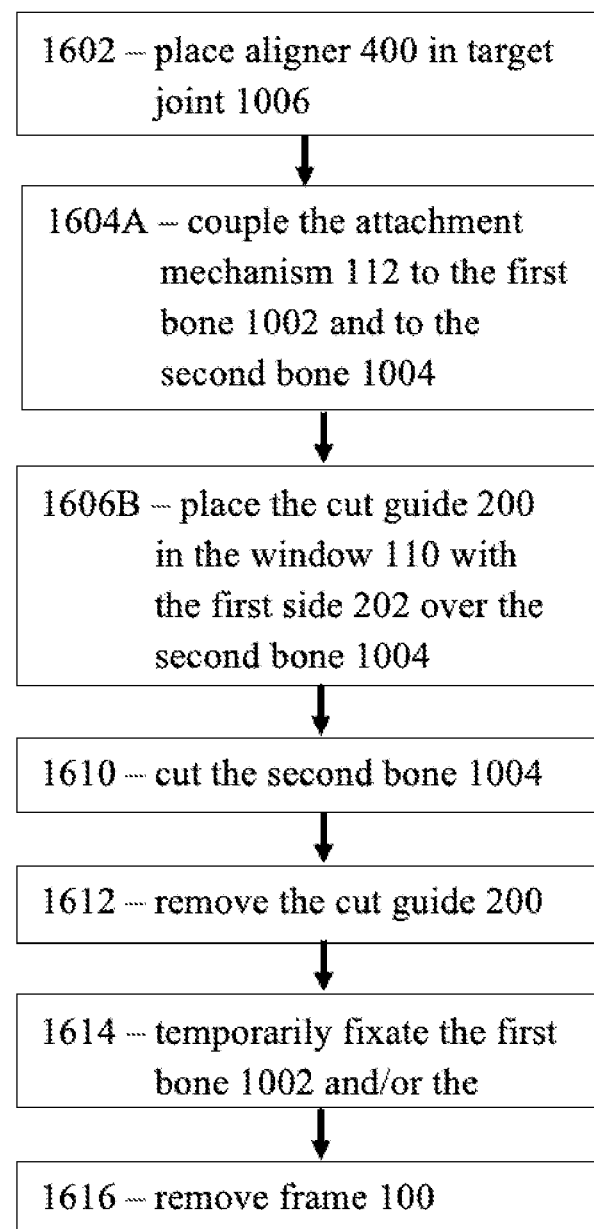

In additional or alternative embodiments, the method of performing an osteotomy (FIG. 16A) can include placing the aligner 400 (coupled to, or integral with, the frame 100) in the target joint 1006 (block 1602) against a cut end of the first bone 1002.

(Block 1604A) The frame 100 can be coupled to the first bone 1002 by coupling the attachment mechanism 112 to the first bone 1002. The frame 100 can be coupled to the second bone 1004 by coupling the attachment mechanism 112 to the second bone 1004.

(Block 1610) The second bone 1004 can be cut by any cutting means. The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

The first bone 1002 and the second bone 1004 can be compressed together and temporary fixation applied (block 1614). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (block 1616). In certain embodiments the frame 100 can be removed after checking bone positions. In other embodiments the frame 100 can be removed before checking bone positions.

The first bone 1002 and the second bone 1004 can be fixed by applying the fixation device 1010 to the first bone 1002 and/or the second bone 1004 (e.g., see FIG. 10H).

In additional or alternative embodiments, the method of performing an osteotomy (FIG. 16B) can include placing the aligner 400 (coupled to, or integral with, the frame 100) in the target joint 1006 (block 1602) against the cut end of the first bone 1002.

The frame 100 can be coupled to the surgical instrument 20 by coupling the attachment mechanism 112 to the surgical instrument 20 (block 1604B).

(Block 1606A) The cut guide 200 can be placed in the window 110, orienting the cut guide first side 202 over the first bone 1002 and the cut guide second side 204 over the second bone 1004 (e.g., see FIG. 10G). In some embodiments the cut guide 200 can be selected from a kit of cut guides 200.

The first bone 1002 can be cut (block 1608) by any cutting means. The first bone 1002 can be cut with the cutting instrument 1008. The cutting instrument 1008 can be held against the cut guide first side 202 to assist in keeping it straight and avoid the cutting instrument 1008 jumping or skiving and damaging bone and/or tissue near the osteotomy site.

If desired, the cut guide 200 can be removed from the frame 100 and bone fragments from the first bone 1002 can be removed from the osteotomy site. The bone fragments can be removed in any suitable manner, such as through the window 110.

(Block 1610) The second bone 1004 can be cut by any cutting means. The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (block 1516). If desired, the bone fragments from the second bone 1004 can be removed by any suitable means, such as, through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

The first bone 1002 and the second bone 1004 can be compressed together and temporary fixation applied (block 1614). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (block 1616). In certain embodiments the frame 100 can be removed after checking bone positions. In other embodiments the frame 100 can be removed before checking bone positions.

The first bone 1002 and the second bone 1004 can be fixed by applying the fixation device 1010 to the first bone 1002 and/or the second bone 1004 (e.g., see FIG. 10H).

In additional or alternative embodiments, the method of performing an osteotomy (FIG. 16C) can include placing the aligner 400 (coupled to, or integral with, the frame 100) in a target joint 1006 (block 1602) against the cut end of the first bone 1002.

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Block 1604A).

(Block 1606A) The cut guide 200 can be placed in the window 110 orienting the cut guide first side 202 over the second bone 1004. In some embodiments the cut guide 200 can be selected from a kit of cut guides 200.

(Block 1610) The second bone 1004 can be cut by any cutting means. The second bone 1004 can be cut with the cutting instrument 1008. The cutting instrument 1008 can be held against the cut guide first side 202 to assist in keeping the cutting instrument 1008 straight and to keep the cutting instrument 1008 from jumping or skiving and damaging bone and/or tissue near the osteotomy site.

The cut guide 200 can be removed from the frame 100 (block 1612). If desired, the bone fragments from the second bone 1004 can be removed by any suitable means, such as, through the window 110.

The first bone 1002 can be moved with respect to the second bone 1004 until the desired configuration is achieved. The first bone 1002 can be moved prior to cutting the first bone 1002 and prior to cutting the second bone 1004. The first bone 1002 can be moved after cutting the first bone 1002 and before cutting the second bone 1004. The first bone 1002 can be moved before cutting the first bone 1002 and after cutting the second bone 1004. The first bone 1002 can be moved after cutting the first bone 1002 and after cutting the second bone 1004.

The first bone 1002 and the second bone 1004 can be compressed together and temporary fixation applied (block 1614). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the techniques that are possible and contemplated herein.

The frame 100 can be removed (block 1616). In certain embodiments the frame 100 can be removed after checking bone positions. In other embodiments the frame 100 can be removed before checking bone positions.

The first bone 1002 and the second bone 1004 can be fixed by applying the fixation device 1010 to the first bone 1002 and/or the second bone 1004 (e.g., see FIG. 10H).

One advantage of the frame 100 spanning the joint is that it allows for good visibility of the joint without removing the frame 100. It also allows for the removal of bone fragments without removing the frame 100. It also allows a surgeon to cut the ideal amount of bone based on patient anatomy because the bones are visible while the cut is being made.

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

What is claimed is:

1. A surgical apparatus comprising:
a first section, a second section, a third section, and a fourth section defining a single quadrilateral window therebetween, wherein:
the first section is configured to align with a metatarsal;
the second section is configured to align with a cuneiform;
the window includes a size configured to span a metatarsal-cuneiform joint when the first section is aligned with the metatarsal and the second section is aligned with the cuneiform to provide surgical access to the metatarsal-cuneiform joint;
the window comprises at least one attachment mechanism coupled to the first section, and at least one attachment mechanism coupled to at least one of the second section, the third section, and the fourth section; and
the first section comprises a first section bottom surface which is configured to conform to the shape of at least one bone; and
the second section comprises a second section bottom surface, and the first section bottom surface is angled at a declination angle relative to the second section bottom surface.

2. The surgical apparatus of claim 1, wherein the attachment mechanism is configured to couple at least one of the second section, the third section, and the fourth section to at least one of a surgical jig and the second bone.

3. The surgical apparatus of claim 1, further comprising at least one radiograph positioning tool.

4. The surgical apparatus of claim 1, wherein the declination angle is configured to be the same as the acute angle formed by the longitudinal axis of the cuneiform and the longitudinal axis of the metatarsal.

5. The surgical apparatus of claim 4, wherein the declination angle is about twelve degrees.

6. The surgical apparatus of claim 1, further comprising a securing device configured to couple the surgical apparatus to a second surgical apparatus.

7. The surgical apparatus of claim 1, further comprising:
a head
including a first end member, a second end member, and a middle member, the middle member comprising a cut guide first side extending from the first end member to the second end member, wherein
the cut guide first side is configured to constrain a cutting instrument in at least one direction;
at least a portion of the head is configured to be encompassed by a single quadrilateral window and the window is sized such that the first end member and the second end member contact two opposing sides of the window; and a securing device configured to couple the cut guide to a second surgical apparatus.

8. The surgical apparatus of claim 7, further comprising a placement device comprising a handle.

9. The surgical apparatus of claim 8, wherein the placement device is coupled to the first end member and extends to the second end member and connects to the second end member.

10. The surgical apparatus of claim 7, further comprising an attachment mechanism including a slot.

11. The surgical apparatus of claim 7, wherein the securing device includes a surface, wherein at least a portion of the surface is configured to conform to at least a portion of the second surgical apparatus.

12. The surgical apparatus of claim 7, wherein the securing device comprises at least one aperture.

13. The surgical apparatus of claim 12, wherein the securing device further comprises at least one screw.

14. The surgical apparatus of claim 7, wherein the head further comprises a head bottom configured to conform to at least one bone.

15. The surgical apparatus of claim 7, further comprising a slot extending along the middle member and configured to accept at least one cutting instrument.

16. The surgical apparatus of claim 1, further comprising an alignment guide configured to align the first section with the metatarsal.

17. The surgical apparatus of claim 16, wherein the alignment guide is removable.

18. A surgical system comprising:
a frame and a cut guide;
wherein the frame comprises:
a first section, a second section, a third section, and a fourth section defining a single quadrilateral window therebetween, wherein:
the first section is configured to align with a metatarsal;
the second section is configured to align with a cuneiform;
the second section comprises a second section bottom surface, and the first section comprises a first section bottom surface that is angled at a declination angle relative to the second section bottom surface;
the window includes a size configured to span a metatarsal-cuneiform joint when the first section is aligned with the metatarsal and the second section is aligned with the cuneiform to provide surgical access to the metatarsal-cuneiform joint; and
the window comprises at least one first attachment mechanism coupled to at least one of the second section, the third section, and the fourth section;
wherein the cut guide comprises a head;
wherein the head is configured to fit within the window and make contact with at least a portion of the first section, the second section, the third section, and the fourth section.

19. The surgical system of claim 18, wherein the cut guide further comprises at least one securing device and the frame further comprises at least one complimentary securing device;
wherein the complimentary securing device is configured to:
conform to the securing device and
couple at least a portion of the cut guide to at least a portion of the frame.

* * * * *